United States Patent
Anderson et al.

(10) Patent No.: US 12,020,823 B2
(45) Date of Patent: Jun. 25, 2024

(54) INTEGRATED VIRTUAL PATIENT FRAMEWORK

(71) Applicant: H. LEE MOFFITT CANCER CENTER AND RESEARCH INSTITUTE, INC., Tampa, FL (US)

(72) Inventors: Alexander Robertson Allan Anderson, Tampa, FL (US); Mark Robertson-Tessi, Tampa, FL (US); Kevin McCash, Tampa, FL (US); Chandler Dean Gatenbee, Tampa, FL (US)

(73) Assignee: H. Lee Moffitt Cancer Center and Research Institute, Inc., Tampa, FL (US)

(*) Notice: Subject to any disclaimer, the term of this patent is extended or adjusted under 35 U.S.C. 154(b) by 792 days.

(21) Appl. No.: 17/126,198

(22) Filed: Dec. 18, 2020

(65) Prior Publication Data

US 2021/0174970 A1    Jun. 10, 2021

Related U.S. Application Data

(63) Continuation-in-part of application No. 15/032,969, filed as application No. PCT/US2014/063341 on Oct. 31, 2014, now abandoned.

(60) Provisional application No. 61/898,990, filed on Nov. 1, 2013.

(51) Int. Cl.
| | |
|---|---|
| *G06Q 50/00* | (2012.01) |
| *G06Q 10/00* | (2023.01) |
| *G16H 10/60* | (2018.01) |
| *G16H 50/20* | (2018.01) |
| *G16H 50/50* | (2018.01) |

(52) U.S. Cl.
CPC ............ *G16H 50/50* (2018.01); *G06Q 50/00* (2013.01); *G16H 10/60* (2018.01); *G16H 50/20* (2018.01)

(58) Field of Classification Search
CPC ........ G16H 50/50; G16H 10/60; G16H 50/20; G16H 20/40
See application file for complete search history.

(56) References Cited

U.S. PATENT DOCUMENTS

| | | | | |
|---|---|---|---|---|
| 2011/0119212 A1* | 5/2011 | De Bruin | ............... | A61B 5/369 706/12 |
| 2014/0114987 A1* | 4/2014 | Hoeng | ..................... | G06N 7/06 707/748 |

* cited by examiner

*Primary Examiner* — Maroun P Kanaan
(74) *Attorney, Agent, or Firm* — Meunier Carlin & Curfman LLC

(57) ABSTRACT

An Integrated Virtual Patient Framework (IVPF) for providing decision support that evolves with increasing data collected on a given patient. Support decisions for patients with limited data is made using statistical prediction tools derived from historical trajectories of similar patients. As patient histories grow, decision support is provided by mathematical models that constrain the possible dynamics of the patient to more detailed predictive models. Weights for each model are assigned depending on uncertainties arising from data fitting and model properties. As new data are entered into a patient record, the models are recalibrated and the weights are adjusted, leading to updated decision support information. The framework also suggests the benefit of additional follow-up data collection events, optimizing the data collection as well as how the IVPF generates predictions. The framework also may present scenarios to patients in a way that informs them of treatment outcomes, given various strategies.

19 Claims, 12 Drawing Sheets

INTEGRATED VIRTUAL PATIENT FRAMEWORK

CROSS-REFERENCED TO RELATED APPLICATIONS

This application in a continuation-in-part of U.S. patent application Ser. No. 15/032,969, filed Apr. 28, 2016, entitled, INTEGRATED VIRTUAL PATIENT FRAMEWORK, which is a U.S. National Stage filing under 35 U.S.C. § 371 of PCT/US2014/63341, filed Oct. 31, 2014, which claims the benefit of priority to U.S. Provisional Patent Application No. 61/898,990, filed Nov. 1, 2013.

BACKGROUND

Conventional applications used in the clinic to inform treatment decisions are typically limited to a single data time point, they are statistically derived, and they accept only limited patient-specific data. These data (i.e., age, tumor grade, tumor size, lymphatic dissemination, etc.) are used to subdivide the entire cohort of patients in the historical record into a sub-cohort that has similar properties as those entered by the clinician. The software then compares outcomes of this sub-cohort according to the treatment they received.

However, these applications have several limitations. First, they can only subdivide patients across parameters which have been measured and recorded in the historical database. Second, they can only give results for therapies which have been used historically on significant numbers of patients. Third, there is no method to use temporal patient-specific data to refine the predicted outcomes.

SUMMARY

The present disclosure describes an Integrated Virtual Patient Framework (IVPF), which is an architecture for optimizing patient-specific clinical decisions that are simulated by mathematical model modules, accomplished directly through a clinical software application. The IVPF provides decision support that evolves with increasing data collected on a given patient by refining weights and models used to determine recommended therapies. The framework also may present scenarios to patients in a way that informs them of treatment outcomes, given various strategies.

In accordance with an aspect of the disclosure, a model-based method for therapeutic decision support in an Integrated Virtual Patient Framework (IVPF) is described. The method includes defining a first disease-specific model, and one or more additional disease specific models that provide therapeutic decision support in accordance with a temporal relationship with multiple timepoints after a patient is diagnosed with a condition; determining, in accordance with each set of patient data at a given time point, a first therapeutic decision by applying a first weight to the first disease-specific model, a second weight to the second disease-specific model, and subsequent weights to the additional disease-specific models; and ranking therapy choices of the first therapeutic decision in a user interface. Thereafter for subsequent patient data received by the IVPF, the following is repeated: adjusting the first weight, second weight and third weight in accordance with the types of subsequent patient data received; comparing the subsequent patient data to virtual patent data in a database of simulated outcomes determined using the first disease-specific model, the second disease-specific model, and the third disease-specific model; determining, in accordance with the comparing, a subsequent therapeutic decision by applying an adjusted first weight to the first disease-specific model, an adjusted second weight to the second disease-specific model, and an adjusted third weight to the third disease-specific model; and ranking subsequent therapy choices of the subsequent therapeutic decision in the user interface.

In accordance with another aspect of the disclosure, a model-based method for therapeutic decision support in an Integrated Virtual Patient Framework (IVPF) is disclosed. The method includes receiving, at a first time, first data associated with a patient; defining at least two disease-specific models that provide the therapeutic decision support in accordance with a temporal relationship with the first time and a second time; determining an initial therapeutic decision by applying weights to a first disease-specific model of the at least two disease-specific models; receiving, at a second time later than the first time, second data associated with the patient; and determining a subsequent therapeutic decision by: comparing the first data and the second data to virtual patients stored in a database of simulations performed in using the at least two disease-specific models; applying weights to the virtual patients to generate a cloud of similar virtual patients to the patient for each of the at least two disease-specific models; and subjecting the similar virtual patients to a trial process using available treatments to determine a range of outcomes; and ranking subsequent therapeutic decisions associated with the outcomes in a user interface.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Overview

Figure 1:
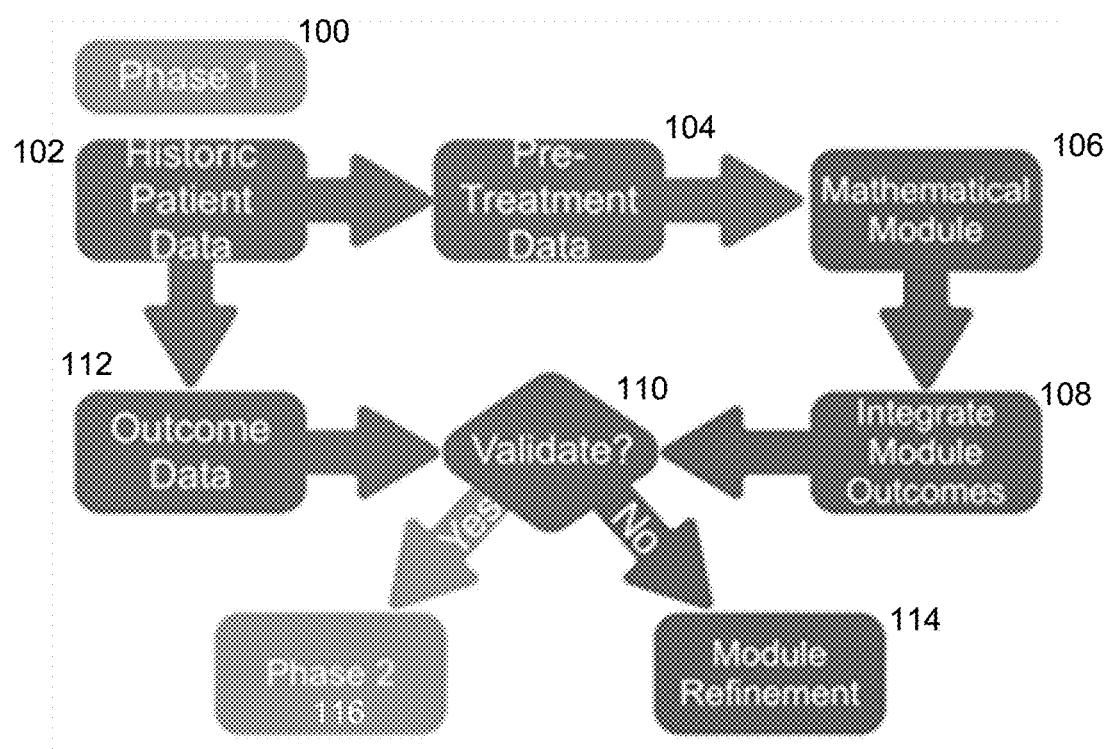
FIG. 1 illustrates a framework to validate outcome predictions of a simulation module against historical data.

The Integrated Virtual Patient Framework (IVPF) of the present disclosure incorporates dynamic and mechanistic modeling to provide for testing of finer patient-specific data subdivisions, and also allows non-standard therapies to be queried for success. In addition, new measurements of patient follow-up data can be rapidly incorporated into the IVPF in order to dynamically update the optimization of the treatment strategy, making the IVPF a powerful tool for implementing adaptive therapies.

Several features of the framework will now be described. The software is accessible to the non-mathematician. This means that inputs, options, and decision recommendations are delivered in a fashion that will have clear meaning to the clinician deciding the treatment. The system is adaptable to the different decision processes which are used in the clinic. These may include discrete decisions (i.e. treat or don't treat; choice between a number of fixed therapy options), continuous decisions (i.e. dosing, scheduling, duration), and hybrid decisions (i.e. combinations of discrete and continuous decisions). Each disease has a particular decision set that the framework will be able to handle. The framework is structured so that the specifics of the biological disease lie within the swappable mathematical modules. This allows for modules to be added, updated, and combined, without affecting the generalized methods used by the framework to inform the clinical decisions.

Term Definitions

As used herein, the following definitions apply to the following terms:

Clinical decision: The overall decision of how to treat the patient. These are specified by one or more control parameters.

Control Parameters: These are the specific treatment parameters that are controllable by the clinician (i.e., type of therapy, dose, duration, etc.).

Optimization criteria: The outcome that is being optimized. Examples include progression-free survival time, curability, drug toxicity, etc.

Historical data: data on a group of patients having a particular disease, such as breast cancer, and any subdivisions of that data.

Pre-decision data: Patient-specific data collected from a clinical patient before the clinical decision is made.

Simulation module (SM): disease specific mathematical model that accepts patient-specific inputs, control parameters, and delivers a metric relevant to the optimization criteria Virtual patient database (VPD): storage for data simulated using the mathematical modules. The database has two parts: an optimized outcome database and a temporal simulation database.

Patient-specific virtual cohort (PSVC): The subset of simulations from the VP database derived from individual patient data, including unknown/unmeasured data.

Risk-reward (RR) controls: variables that are controlled by the user in the software interface to allow for clinician input on the weight of various factors in the optimized results.

Example Workflow

With reference to FIGS. 1-4, in accordance with aspects of the present disclosure, the IVPF may operate in four phases: (1) validate the module, (2) populate the databases, (3) optimize the initial clinical decision for individual patients, and (4) prospectively track and refine individual patient treatment and outcome predictions. The first two phases are performed before the system is used in the clinic. This foundation is then used for rapid initial decision making in Phase 3 and subsequent patient tracking and dynamic therapy optimization in Phase 4.

A brief description of the phases is given here, followed by additional details.

Phase 1: Module validation. In this phase, the framework is used to test the predictions of a simulation module developed for the IVPF. These simulated outcomes are compared with historical outcomes for actual patients.

Phase 2: Module analysis and database population. Once the module is validated, the IVPF uses the module to generate a database of outcomes that can be called upon to determine optimal clinical decisions in Phase 3. Temporal data is stored for use in the adaptive therapy of Phase 4.

Phase 3: Initial diagnosis and therapy optimization. A clinician inputs patient-derived pre-decision data into a software application. The clinician also chooses acceptable levels of risk related to the patient's potential treatment plan, which can include risk of treatment failure, toxicities, patient compliance, co-morbidities, etc., through the setting of one or more risk-reward sliders. The IVPF uses this information to parse the outcomes in the VP database in real time and derive predictions for a patient-specific virtual cohort that inform the actual clinical decision.

Phase 4: Prospective patient tracking and dynamic therapy optimization. The IVPF tracks each individual clinical patient by using existing patient data and the mathematical module(s) to generate detailed patient-specific temporal outcomes for the therapy chosen in Phase 3. At the time when follow-up data is collected (i.e., blood work, imaging, biopsies, toxicity reports, etc.), this temporal data is used to further refine the PSVC of the patient. Additionally, new settings for risk-reward sliders can be applied given the clinicians objective response to the therapy to date. These new data and clinician inputs will lead to updated predictions of subsequent optimal therapy.

Prior to the implementation in the IVPF, each simulation module is developed for the particular disease and relevant clinical decision(s). The development of a particular SM is not directly part of the IVPF. The IVPF does not specify the methods used to model the disease. However, the SM may satisfy the following requirements so that they work within the IVPF:

(i) The SM outlines the range of all inputs and control variables, and also provides one or more output metrics;

(ii) The SM provides information on any additional risk-reward metrics particular to the disease in question;

(iii) For validation, a relevant dataset of outcomes pertaining to the disease in question is provided, with inputs and outputs relevant to the SM. In other words, the SM should be directly comparable to an output metric derived from clinical cohort studies.

A detailed description of Phases 1-4 will now be provided. Referring now to FIG. 1, there is shown a framework 100 for Phase 1 of the IVPF. In Phase 1, the IVPF uses a mathematical simulation module 106 to validate the outcome predictions of the module against historical data 102 and pre-treatment data 104. At The IVPF will call on the module 106 to simulate the patients in the historical dataset, subject to any measured patient data and control parameters. Unknown parameters may be varied throughout the range accepted by the module. This will produce a historical virtual patient cohort (108). The outcomes predicted for the historic virtual cohort will be compared to the true historical outcomes (112) in a validation 110. If the validation is not a statistically accurate representation of the actual outcomes observed in the historical data, the module would be returned for additional development 114. Once a satisfactory validation has been achieved for the module, Phase 1 would be complete and the module would be ready to move to Phase 2 (116).

Alternatively, the module 106 could be extended to predict additional patient specific parameters which would improve the prediction of patient outcomes. This Phase 1 extension would essentially be performed with additional data collection followed by repeated validation.

An example of how a series of modules would be validated and extended to incorporate additional parameter effects will not be described. In order to illustrate how the IVPF might be used to predict and validate the effect of new patient-specific measurements, we have constructed some historical data for a generic disease. In this historical patient cohort, the patient-specific parameter p1 is measured as either hi or low. In addition, there is historical outcome data on these patients subject to three therapeutic options. The patients were either given therapy A, therapy B, or no therapy. The outcome metric (i.e., five-year survival) for this historical data is shown in table 1, where a higher outcome percentage is better.

TABLE 1

Historical true patient data with p1 measurement,
for three therapeutic options
Measuring P1 only

|  | p1 lo | p1 hi |
|---|---|---|
| Rx A | 7.5 | 39.25 |
| Rx B | 1.25 | 46.25 |
| Ctrl | 3 | 20.5 |

In Table 1, patients with low p1 (left column) have very poor outcomes regardless of the therapeutic approach. Patients with high p1 (right column) are more responsive to all three therapeutic options. The historical data would suggest that therapy A is the best choice when p1 is low, and therapy B is the best choice when p1 is high.

Suppose a mathematical model module is built to simulate the disease and optimize therapies, labeled Module 1. The module uses three parameters as inputs, p1, p2, and p3, each of which can be either high or low. The combinations of these three parameters leads to eight patient types. The IVPF would begin by simulating these eight types of patients, combined with receiving one of the three therapeutic options. This leads to twenty-four outcomes for the patients. These data are shown in Table 2, with each column representing a patient class as delineated by the parameter settings shown in the bottom three rows.

TABLE 2

Simulated patient data using Module
1, for three therapeutic options

| Treatment | Model No. 1 | | | | | | | |
|---|---|---|---|---|---|---|---|---|
| Rx A | 14 | 5 | 22 | 4 | 88 | 65 | 94 | 64 |
| Rx B | 22 | 7 | 25 | 5 | 55 | 23 | 43 | 26 |
| Ctrl | 5 | 2 | 4 | 2 | 21 | 16 | 18 | 12 |
| p1 (meas) | lo | lo | lo | lo | hi | hi | hi | hi |
| p2 (unk) | lo | lo | hi | hi | lo | lo | hi | hi |
| p3 (unk) | lo | hi | lo | hi | lo | hi | lo | hi |

The data in Table 2 cannot be compared directly to the historical data of Table 1 because the values of p2 and p3 are not known in the historical data. Therefore, the IVPF integrates across the dimensions of p2 and p3 to derive a comparison dataset from the simulated data. This would generate Table 3. In this simple case, all four data points for p1 low in Table 2 for each therapy are averaged, leading to six data points in Table 3.

A validation check between the simulated outputs of Table 3 and the historical outcomes of Table 1 would show that this first model is not a good prediction tool. The simulation results do not predict the right therapy for either p1-high or p1-low groups. In addition, it significantly overestimates the outcome data for several groups of patients. This module would fail the validation step of Phase 1 and be returned for further development.

TABLE 3

Simulated patient data using Module 1, integrated across p2 and p3 data
Model: Measuring P1 only

|  | p1 lo | p1 hi |
|---|---|---|
| Rx A | 11.25 | 77.75 |
| Rx B | 14.75 | 36.75 |
| Ctrl | 3.25 | 16.75 |

After further development the new model, Module 2, is submitted to the IVPF. Again the IVPF performs a new validation check as described for Module 1, and generates Table 4.

TABLE 4

Simulated patient data using Module 2 for three therapeutic options

| Treatment | Model No. 2 | | | | | | | |
|---|---|---|---|---|---|---|---|---|
| Rx A | 24 | 19 | 5 | 4 | 65 | 29 | 48 | 5 |
| Rx B | 1 | 0 | 1 | 5 | 86 | 51 | 12 | 41 |
| Ctrl | 1 | 2 | 4 | 2 | 22 | 19 | 8 | 5 |
| p1 (meas) | lo | lo | lo | lo | hi | hi | hi | hi |
| p2 (unk) | lo | lo | hi | hi | lo | lo | hi | hi |
| p3 (unk) | lo | hi | lo | hi | lo | hi | lo | hi |

Again the IVPF integrates across the unknown dimensions of parameters p2 and p3 to generate Table 5, segregated by patient p1 values.

TABLE 5

Simulated patient data using Module 2, integrated across p2 and p3 data
Model: Measuring P1 only

|  | p1 lo | p1 hi |
|---|---|---|
| Rx A | 13 | 36.75 |
| Rx B | 1.75 | 47.5 |
| Ctrl | 2.25 | 13.5 |

This module satisfies the validation step, as it predicts the historical data of Table 1 with significant accuracy. Module 2 could then be sent forward to Phase 2 of the IVPF for analysis, database population, and eventual clinical use. Here, we use Module 2 to describe the auxiliary Phase 1.5, in which the validated module is used to predict novel patient measurements that can further refine the outcome predictions.

By using the full simulation data from Table 4, the IVPF can check to see which combinations of parameter measurements would give additional outcome segregation. By integrating only across p3 and p2, the following two outcome tables in Table 6 can be generated.

TABLE 6(a)

Simulated patient data using Module 2, integrated across p3 data.
Measuring p1 and p2

|  | lo/lo | lo/hi | hi/lo | hi/hi |
|---|---|---|---|---|
| Rx A | 21.5 | 4.5 | 47 | 26.5 |
| Rx B | 0.5 | 3 | 68.5 | 26.5 |
| Ctrl | 1.5 | 3 | 20.5 | 6.5 |

TABLE 6(b)

Simulated patient data using Module 2, integrated across p2 data.
Measuring p1 and P3

|  | lo/lo | lo/hi | hi/lo | hi/hi |
|---|---|---|---|---|
| Rx A | 14.3 | 11.5 | 56.5 | 17 |
| Rx B | 1 | 2.5 | 49 | 46 |
| Ctrl | 2.5 | 2 | 15 | 12 |

The data from Table 6 suggest that measuring p2 would have little advantage. For patients with p1-high, the suggested therapy would remain treatment B, so p2 would not alter the clinical decision. However, panel (b) of Table 6 shows that the measurement of parameter p3 would segregate patients with p1-high into two groups with different optimal therapy. For p1-high, p3-low patients, therapy A is now preferable to therapy B. Patients with both p1-high and p3-high would do better to receive therapy B.

In order to validate these results, it would be necessary to collect p3 data from patients and observe their outcomes. In some cases, this may be retrievable from the original dataset, in the case where tissue samples, gene sequencing, or imaging have been retained but not analyzed. In other cases, it may involve a prospective study on new patients. In either case, this new data will generate a more detailed historical outcome data. Table 7 shows the expansion of the Table 1 data to account for differences in p3 in patients.

TABLE 7

Historical patient data, measured for p1 and p3
Measuring p1 and P3

|  | lo/lo | lo/hi | hi/lo | hi/hi |
|---|---|---|---|---|
| Rx A | 9 | 6 | 56 | 22.5 |
| Rx B | 1 | 1.5 | 65 | 27.5 |
| Ctrl | 4 | 2 | 35.5 | 5.5 |

Unfortunately, the predictions of Module 2 have been disproven by the additional data collection. The p1-high, p3-low group is still better with receiving therapy B, and not therapy A as predicted. Therefore, Module 2 would be rejected for fit and returned for further development.

Finally, Module 3 is developed. In this case, the module produces the data shown in Table 8. Module 3 can be compared to the historical data for both p1 and p3 from both Table 1 and Table 7 using similar integration techniques as before, giving rise to Table 9. In this case, the module satisfies both the historical data for p1 only, and for p1 and p3 together, as seen in Table 9, panels (a) and (e) respectively. Furthermore, the module predicts that the measurement of p2 would be useful for additional patient segregation (panel (d)).

TABLE 8

Simulated patient data using Module 3 for three therapeutic options

| Treatment | Model No. 3 | | | | | | | |
|---|---|---|---|---|---|---|---|---|
| Rx A | 6 | 11 | 12 | 2 | 74 | 37 | 36 | 2 |
| Rx B | 2 | 0 | 3 | 1 | 75 | 15 | 48 | 37 |
| Ctrl | 0 | 0 | 0 | 0 | 41 | 12 | 26 | 7 |
| p1 (meas) | lo | lo | lo | lo | hi | hi | hi | hi |
| p2 (unk) | lo | lo | hi | hi | lo | lo | hi | hi |
| p3 (unk) | lo | hi | lo | hi | lo | hi | lo | hi |

TABLE 9(a)

Simulated patient data using Module 3, integrated
across pairs of parameters.
Measuring P1 only

|  | p1 lo | p1 hi |
|---|---|---|
| Rx A | 7.75 | 37.25 |
| Rx B | 1.5 | 43.5 |
| Ctrl | 0 | 21.5 |

TABLE 9(b)

Simulated patient data using Module 3, integrated
across pairs of parameters.
Measuring P2 only

|  | p1 lo | p1 hi |
|---|---|---|
| Rx A | 32 | 13 |
| Rx B | 22.75 | 22.25 |
| Ctrl | 13.25 | 8.25 |

TABLE 9(c)

Simulated patient data using Module 3, integrated
across pairs of parameters.
Measuring P3 only

|      | p1 lo | p1 hi |
|------|-------|-------|
| Rx A | 32    | 13    |
| Rx B | 32    | 13    |
| Ctrl | 16.75 | 4.75  |

TABLE 9(d)

Simulated patient data using Module 3, integrated
across single parameters.
Measuring p1 and P2

|      | lo/lo | lo/hi | hi/lo | hi/hi |
|------|-------|-------|-------|-------|
| Rx A | 8.5   | 7     | 55.5  | 19    |
| Rx B | 1     | 2     | 44.5  | 42.5  |
| Ctrl | 0     | 0     | 26.5  | 16.5  |

TABLE 9(e)

Simulated patient data using Module 3, integrated
across single parameters.
Measuring p1 and P3

|      | lo/lo | lo/hi | hi/lo | hi/hi |
|------|-------|-------|-------|-------|
| Rx A | 9     | 6.5   | 55    | 19.5  |
| Rx B | 2.5   | 0.5   | 61.5  | 25.5  |
| Ctrl | 0     | 0     | 33.5  | 9.5   |

TABLE 9(f)

Simulated patient data using Module 3, integrated
across single parameters.
Measuring p2 and P3

|      | lo/lo | lo/hi | hi/lo | hi/hi |
|------|-------|-------|-------|-------|
| Rx A | 40    | 24    | 24    | 2     |
| Rx B | 38.5  | 7     | 25.5  | 19    |
| Ctrl | 20.5  | 6     | 13    | 3.5   |

Once again, additional data collection on p2 values in patients would be derived to check for validation. The historical data would generate Table 10, showing that the model successfully predicts for the segregation of optima due to p2 status.

TABLE 10

Historical patient data, measured for p1 and p2
Measuring p1 and P2

|      | lo/lo | lo/hi | hi/lo | hi/hi |
|------|-------|-------|-------|-------|
| Rx A | 8.5   | 6.5   | 51    | 27.5  |
| Rx B | 1.5   | 1     | 45    | 47.5  |
| Ctrl | 2     | 4     | 25    | 16    |

Module 3 would therefore satisfy the validation criteria for parameters p1, p2 and p3 and therefore could proceed to Phases 2 and 3 in order to assist with individual patient-specific clinical decision-making.

This highly simplified example above illustrates the process of using the IVPF to predict and validate module outcomes based on patient-derived data. Though it may seem like the results only reproduce the historical data, this is because the example restricted itself to a few binary parameters and therapies. The actual modules to be used in the IVPF are likely to include continuous variables for both patient measurements and therapy options, and therefore the results will be significantly more complex. However, the same process can be used for continuous variables with this integration and validation approach.

Figure 2:
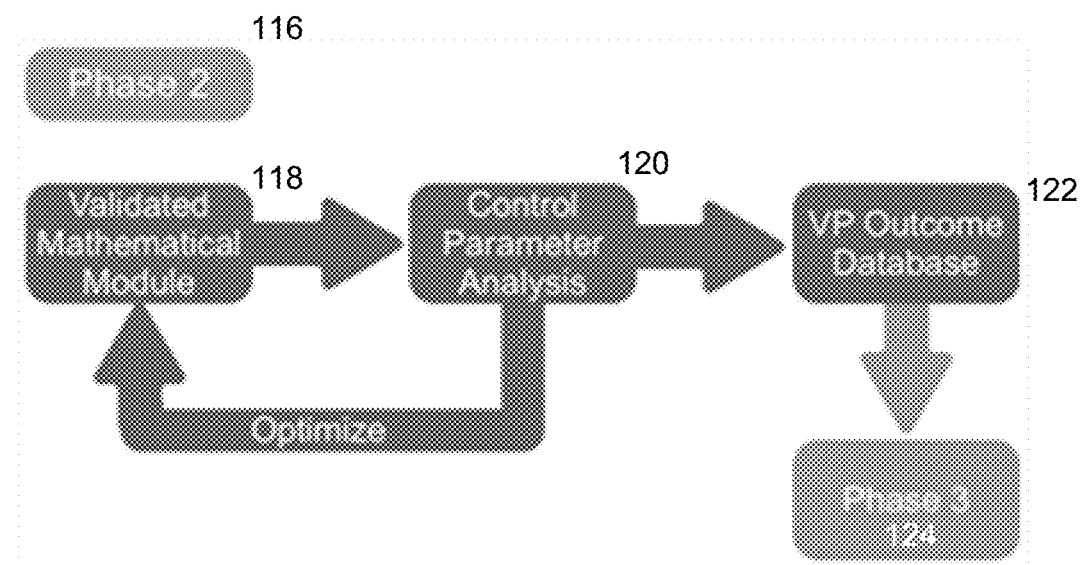
FIG. 2 illustrates a framework for use a validated module to populate a virtual patient database of optimal clinical outcomes.

With reference to FIG. 2, there is illustrated a framework for Phase 2 (116), where the IVPF will use the validated module 118 to populate a virtual patient database 112 of optimal clinical outcomes. This VPD will cover an entire cohort of virtual patients spanning the complete range of possible patient-specific data and clinical controls (120) that are accepted by the SM. These data will be stored in a way that the IVPF can rapidly aggregate them for delivery of results to the clinical user in Phase 3 (124). Additionally or alternatively, temporal data can be stored in this phase for possible use in Phase 4 (140), depending on storage capabilities.

Figure 3:
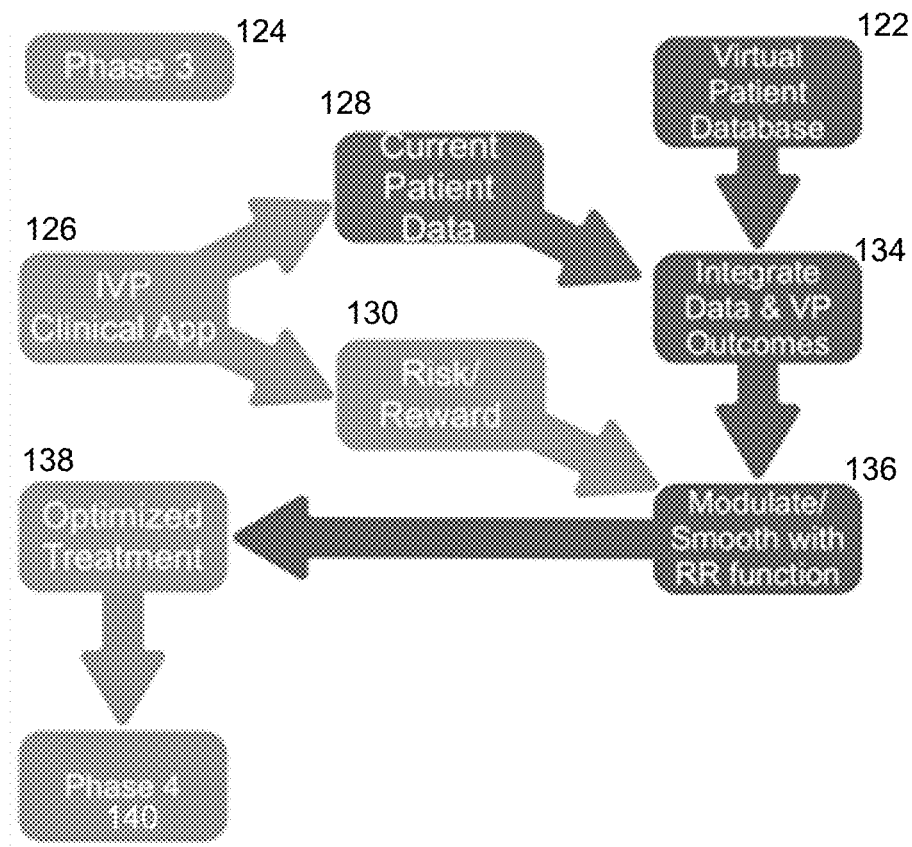
FIG. 3 illustrates a framework for performing an initial clinical diagnosis and therapy optimization.

With reference to FIG. 3, there is illustrated a framework for Phase 3 (124) wherein there is performed an initial clinical diagnosis and therapy optimization. The outcomes in the VP database 122 developed in Phase 2 (116) may be used by the IVPF to rapidly derive initial patient-specific recommendations in the clinic. This may be accomplished, for example, through a clinical application 126 that accepts patient data 128 and treatment criteria 150. Other interfaces and application may be used to achieve the functions described herein. The IVPF uses the inputs from the clinician to analyze the database and outcomes (134), smooth the data (136) and generate optimal recommendations (138) for therapy. The process may then move to Phase 4 (140).

As a non-limiting example of Phase 3, a patient enters the clinical pathway, and proceeds through the usual standards of diagnosis and patient data collection, including patient history. This forms the pre-decision data. The patient is assigned a virtual patient ID in the IVPF. The clinician would select the appropriate module(s) relevant to the disease in question and suitable for informing the clinical decision at hand. The clinician would select one or more optimization criteria. Restrictions to the control parameters would be made at this time. For example, a clinician may exclude a particular type of therapy from the options of the module, for patient-specific reasons.

The module(s) will have certain input specifications, and these will be derived from the pre-decision data where known, and input into the software application by the clinician. This input will immediately place the real patient into a patient-specific virtual cohort with parameters in the same range as those of the patient. The IVPF will then automatically use the virtual patient database to determine the optimal values of the control parameters. As described earlier, these could be as simple as a binary decision, or as complicated as determining the sequence and dosing of a mix of several drugs.

The results will be presented to the clinician in an information panel displayed on a software application. A feature is that the interface will be interactive. The clinician can interrogate the results on many different levels, to understand the implications of the various optimal therapies that are being presented to them. By further varying therapeutic conditions and any risk-reward values, the clinician will have a feel for how sensitive the predictions are for the particular patient and the associated diagnostic and care-related factors.

The results presented on the interface may be statistical in nature, based on the selected optimization criteria. If appropriate to the clinical decision, several options can be compared to standard of care (SOC) results. The results will be variable depending on the settings of one or more risk-reward sliders. These sliders control the sensitivity of the optimization algorithm to include the risk of predictive error due to various clinical and algorithmic factors. These sliders may include, but are not limited to, the risk of errors in therapeutic administration; the risk of patient miscompliance with therapeutic regimen; the risk of drug toxicity; the risk of promoting existing or potential co-morbidities; risk of errors in the measurement of patient data; stochastic effects in the SM; the effect of highly variable outcome landscapes in the SM output. Additional details are in the technical implementation section.

A feature of the present disclosure is the ability of the clinician to interact with the results in real time through the setting of therapeutic control restrictions and values of risk-reward weighting. This real-time analysis is performed using the VPD and the associated analysis tools described herein. Example user interfaces implementing this feature are described below with reference to FIGS. 11 and 12. Since mathematical models take time to simulate, real-time analysis of a given SM may not be possible if simulations have to be run for each patient at the time of diagnosis. Furthermore, real-time interaction with the results also may not be possible without the framework of a populated database that is analyzed with integrating tools. The variation of optimized predictions due to one or more clinician inputs depends on the example framework and equivalents that are proposed herein.

When applicable, the IVPF will suggest that the measurement of additional patient data could lead to a more refined prediction. For example, if the patient is in a virtual cohort where treatment outcomes are sensitive to a particular molecular expression that has not been measured in this particular real patient, then measurement of this marker in histological sections could lead to improved predictions from the IVPF. The clinician would then decide whether or not to measure the additional data, if possible, for a subsequent reanalysis of the clinical decision.

Once the clinician receives the results from the IVPF software interface, they would make a final decision on the treatment strategy. This actual decision would then be input into the IVPF, and the patient enters into Phase 4 (140).

Figure 4:
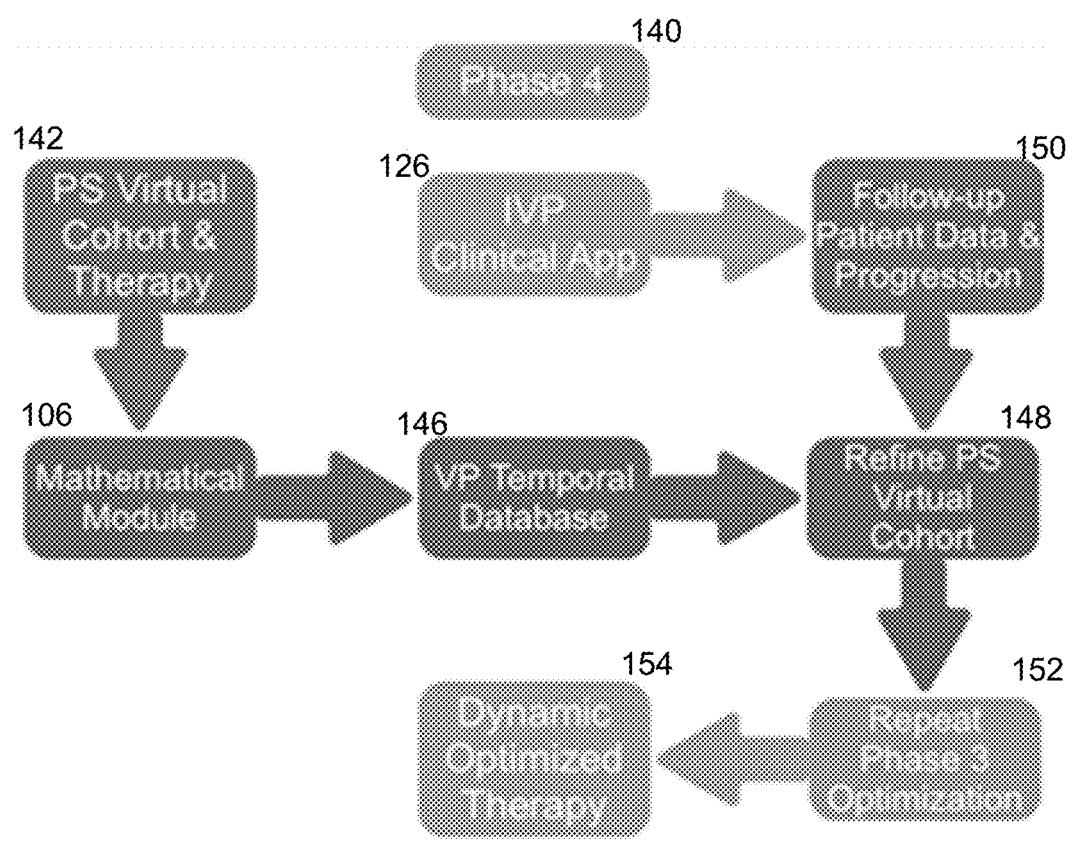
FIG. 4 illustrates a framework for prospective patient tracking and dynamic therapy optimization.

FIG. 4 illustrates there is illustrated a framework for Phase 4 (140), where prospective patient tracking and dynamic therapy optimization is performed. Phase 4 of the IVPF will serve as a patient-specific tracking and prediction system, delivering dynamically optimized therapy recommendations for each patient on an individual basis. Unlike current tools which use only an instantaneous snapshot of the patient to derive a single prediction, this framework explicitly uses temporal patient data to refine therapeutic predictions and minimize the risk of treatment failure. If there are any variations in the protocol of therapy chosen at diagnosis, e.g. a patient misses a dose, or changes their appointment, this information can be input to the IVPF for an immediate analysis of the implications for optimal therapy, based on the information contained in the VPD. The risk-reward analysis will provide a new assessment of the risk for any particular negative event, and furthermore therapeutic changes to improve the risk-reward balance may be suggested by the framework.

For example, in Phase 4, once the treatment decision has been chosen in Phase 3, the IVPF calls on the math module 106 to perform simulations of future outcomes under this therapy for the patient-specific virtual cohort 142. The temporal data from these simulations are stored in the VP database 146 so that it can be directly compared with real data gathered from the patient, either at the next follow-up visit or from remote patient reporting.

When new patient data are available, the additional data 150 collected from the patient are input into the IVPF app 126. By comparing these data with stored temporal simulation data, the patient-specific virtual cohort can be further refined (at 148) to exclude those areas of the cohort that do not match the true progression of the patient. The integration and optimization described in Phase 3 is used (at 152) to deliver new optimal treatment strategies 154 with this refined VP cohort. These updated recommendations are returned to the clinical user in order to inform the choice of follow-up treatment. Further refinement of the risk-reward (RR) sliders, based on objective clinical observation of the patient response to date, can be performed by the clinician at this point. The clinician would then make a decision on the continuing course of therapy, which may be to remain on the original therapeutic regimen, or modify in accordance with new predictions. Once the follow-up therapy is chosen, this may again be input into the IVPF to generate new temporal data. Phase 4 may be repeated as necessary for each follow-up visit until the care has been completed.

The virtual patient database generated from the simulation model will be greatly enhanced over time as patient specific data is generated in the clinic and used to both populate the VPD and validate specific results. In other words, the actual data gathered from patients can be used to continually refine the weighting algorithm across parameters and variables that were previously unmeasured in historical datasets. This feed-forward approach allows for better predictions to be made for subsequent patients entering the system. The trajectory of each patient specific virtual cohort within the greater space of all virtual patients can be used to analyze the biological factors prevalent in the disease, therefore shaping likelihood distributions for unmeasured/unmeasurable parameters. For example, an unmeasurable patient parameter such as micrometastatic burden might eventually be calculated as a likely distribution by the IVPF by analyzing the possible burdens associated with previous patients, as determined by the refinement of VP cohorts and associated outcomes.

This process of algorithm improvement will be accomplished by implementing a machine learning environment, where the algorithms used to deliver optimal strategy will be analyzed to compare virtual patient weighting distributions and actual patient distributions. This comparison can lead to adjustments of the weighting algorithms, if there is a discrepancy between the real and assumed distributions. A similar process could be used to refine the effects of therapy as determined by the SM. Machine learning can check for skewed results that are consistently offset from the true results, suggesting weighting imbalances in the optimization and risk-reward algorithms.

Example Environment

Figure 5:
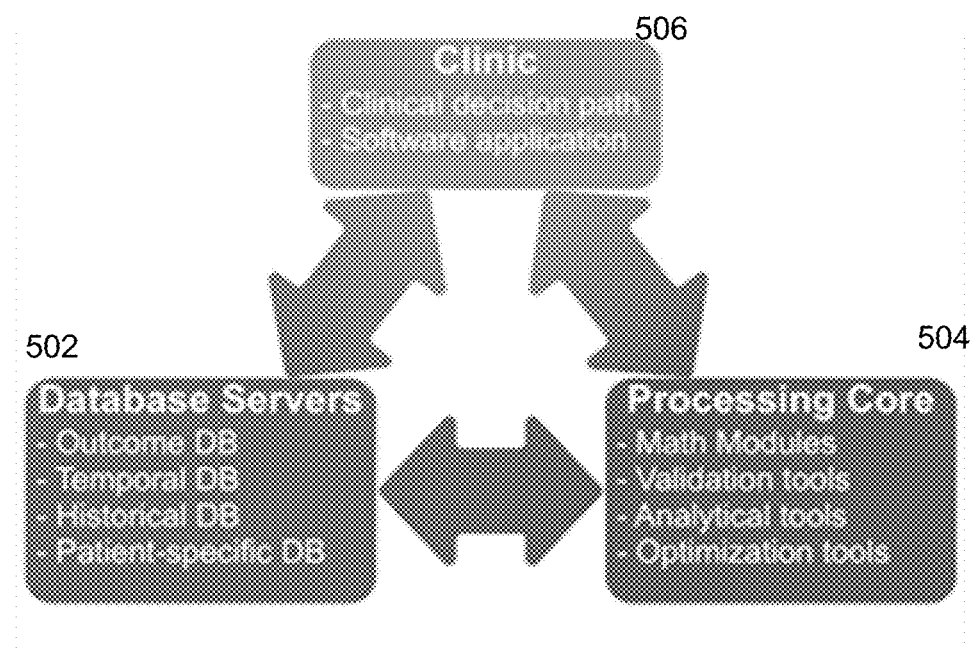
FIG. 5 is a schematic block diagram of the components of an IVPF environment.

FIG. 5 is a schematic block diagram of the components of the IVPF environment 500. The IVPF may include a processing core 504, database servers 502, and a clinical device 506 running the interface application 126 to implement the four phases described above. The implementation IVPF within the environment 500 may operate in four layers. The first, innermost layer is a disease-specific simulation module. This may be developed for specific diseases by biologists, clinicians, mathematicians and/or statisticians to simulate a particular aspect of the disease. Examples may include a model of tumor growth, a model of drug pharmacokinetics and diffusion into the disease site, etc.

The second layer is the virtual patient database 122 within the database servers 502. The database 122 may be divided into two main sections: standardized outcome data and temporal data. An optimized outcome database is a collection of optimal outcomes produced by using the simulation modules, encompassing the broad spectrum of possible patients and treatments relevant to the module in question. The temporal simulation database is where patient-specific simulations for specific treatment strategies are stored for use with follow-up data from each patient using the system.

The third layer is the simulation database integrator and optimizer. The integrator will take patient-specific data to combine the results contained within the virtual patient database, producing results relevant to a patient-specific virtual cohort, which is smaller than the entire virtual cohort. Additionally, the integrator can use temporal results from patient follow-up data to further refine the patient-specific virtual cohort. The optimizer uses the patient-specific subset of data to determine the optimal decision based on the restrictions of control parameters and other clinical considerations.

The fourth layer is the clinical interface application. This is software that allows the clinical user to select the modules, input initial and follow-up patient-specific data, restrict the treatment and optimization criteria, set risk-reward values, and view the results of the IVPF predictions.

Simulation Modules

Below is a more detailed discussion of the simulation modules implemented within each of the layers above. In layer 1, the simulation modules may have a specific format for usability in the other layers of the IVPF. First, they may accept as inputs two classes of data. One class of input data is patient-specific biological measurements, denoted I. The second class of data is clinically-adjustable control parameters, denoted R. Both forms of inputs may only be permitted within an acceptable domain, defined by the simulation module. With a given definition of inputs, (I, R), the module then exports one or more optimization metrics. The optimization metrics are informative of each desired optimization criteria as derived from clinical practice. In this framework, the modules act as functions of I and R and return the optimization metric(s).

Each module may specify the following:
Input parameters (I):
  Domain: Each input parameter is assigned a biologically permissible domain. The domain is bounded and can be discrete or continuous. Possible examples:
    Number of cells at time of therapy: A discrete parameter with integer values between 1 and $10^{12}$ inclusive
    Age: A continuous variable between 0 and 125 years
    Sex: A discrete variable with two options (i.e., 0 and 1)
    Biomarker expression: a continuous variable with range 0% to 100%
    Production rate of a cytokine: a continuous variable from 0 to 1.3 mM/day
  Distribution: Each parameter domain is accompanied by a probability distribution function (PDF). This describes the expected values of the parameter. The distribution is used for sampling the domain of the parameter when a precise measurement is not known. The default PDF is linear over the domain.
  Input parameters need not be measured or even measurable at the time of module development
Control parameters (R):
  Each clinical parameter is directly derived from a controllable clinical therapeutic variable.
  Domain: The domain of clinical control parameters is identified and bounded
Module outputs
  Optimization metrics: these output data are the results that will be used by the integrator and optimizer for deriving virtual patient cohort statistics. The output can be a continuous metric, or a discrete outcome. Examples:
    Remission time
    Toxicity measure
    Cured/not cured
    High, medium, low risk
  Domain error code: indicates that the generated input call is outside of the bounds of the model's use. This is for cases where the input domains are dependent on each other. This flag will tell the database to ignore these results.

In layer 2, the VPD may be split into two datasets: (1) the optimized outcome database, and (2) the patient-specific temporal simulation database. Though both databases operate in the same multi-dimensional parameter space defined by the particular mathematical module, the methods of populating the databases are different because of the distinct clinical needs of Phases 3 and 4.

The Optimized Outcome Database

The optimized outcome database, a subset of the VPD, is generated so that it will be useful to any possible patient that enters the clinic for the first time. Therefore the database has to cover the entire space of parameters and therapy options. Since complete analysis of the entire space each time a new patient enters the system is prohibitive, we instead propose a sparse but intelligently-generated optimized outcomes database so that the space can be reconstructed rapidly enough to deliver a real-time recommendation for a specific patient. The database may, for example, be populated by a combination of a genetic algorithm and variable-step-size iterative method. Since the dimensionality of inputs accepted in a simulation module can be very high, the approach of using fine-grained simulation of all points in a discretized input-parameter space is likely to be prohibitive both in terms of data storage and the time needed to simulate such a system. Therefore, an adaptive-step-size approach may be chosen. The goal of the database generator is to establish the locations of local optima and gradient strengths along each dimension of input data. As more simulations are run with the module, the database would continue to accumulate points in the range of outputs, lending more detail to the landscape of each optimization metric.

For a given module, Layer 2 will generate an outcome database. During Phase 2, the outcome database will be populated across the full permissible range of input and output parameters, so that the clinical tool in Phase 3 need only query previously run simulations to find outcomes for optimization relative to patient-specific data.

Two main processes can be used to populate the database:
  Coarse-grained simulations across the grid of input and control parameters
    This approach gives a sampling of the range of the module output
    The step size will be variable in each dimension, and dependent on the gradient of the output metric The goal is to characterize not only areas of good and bad metric values, but also to find areas where the slope may be high. High slope of the output metric corresponds to higher risk in giving treatments within that range of control parameters A genetic algorithm (GA) to find the optimal control parameters R¬opt in the space of I This second approach will seek optimal therapy within the space of I using a genetic algorithm. The process will generate a list of sequentially less optimal control parameters R¬opt in each hyperplane of I. These serve as the foundation for additional simulations in the area of the optimum in order to find the risk gradient associated with the optima The GA will use mutation and recombination of the control parameters to converge on local minima Gaussian exclusion will be used to find subsequent minima in the space, until the required number of minima have been found All simulations may be stored in a managed database that is able to be restricted to any range of input and control parameters. These processes occur independently for each output metric supported by the module. The complexity of the model will dictate the necessary simulation resolution achievable in such a database.

The Temporal Simulation Database

The temporal simulation database, a subset of the VPD, contains time-course data generated by simulations for a specific patient. When the initial patient therapy is decided at the end of Phase 3, this information fixes the control parameters for the patient. The IVPF will then use the mathematical module to generate simulations that predict the time-course of patients contained within the patient-specific virtual cohort subject to the administration of the actual therapy decided by the clinician. In this case, the algorithm will start with a coarse-grained sampling of the cohort parameter space, and then continue to add finer sampling until the patient returns for follow-up diagnosis. The simulation data is stored with a temporal resolution that would be relevant to typical follow-up times. In other words, a disease where the follow-up times are spaced apart by 6-12 months would not need a temporal resolution of days, whereas a fast-progressing disease that requires weekly monitoring may require temporal resolution on the order of one day or less. These criteria are module-specific and would be determined in the development of the module.

When the temporal simulation database is populated, corresponding outcomes are stored in the optimized outcome database. This will permit dynamically optimized therapy decisions to be rapidly made during patient follow-up.

In layer 3, the database integrator may use the virtual patient outcome database to generate a subset cohort of virtual patients. This cohort is generated through the input of data (P) from a single clinical patient, entered through the clinical interface application. This patient-specific data P will restrict the multi-dimensional domain of the set of parameters I, and generate a correspondingly smaller subset of outcome data (the patient-specific virtual cohort). This derivation will include an interpolation algorithm on the dimensions of R followed by an integration algorithm across the dimensions of P, with the possible use of weighting if applicable. Finally, the integrated data is smoothed according to the risk-reward inputs provided by the user to determine a suitable set of optimal recommendations for the specific patient, based on the individual patient data which has been input.

The interpolation algorithm will take the optimum data points stored in the simulation database and construct a function (g(P,R)) composed of multiple Gaussian curves with heights corresponding to the value of the optimization metric at each position in R corresponding to an optimum. Each point in the restricted domain of P with existing simulation data will have such a function. The integration algorithm will then combine these functions with the appropriate weighting function for each parameter value in P. In other words, the Gaussian functions g will be multiplied by the weights attached to the space P and then summed. This produces the patient-specific outcome function, which incorporates the uncertainty in P across the effects of control parameters R. Once this function is generated, it is smoothed by the selected values of the risk-reward sliders, such that lower values of risk-reward correspond to greater smoothing of the outcomes across the dimensions relevant to the particular risk being calculated. This smoothed function is analyzed to determine the maxima, and these maxima are ranked to form the basis of the recommendations for control parameters R_opt that are returned to the user.

Figure 6:
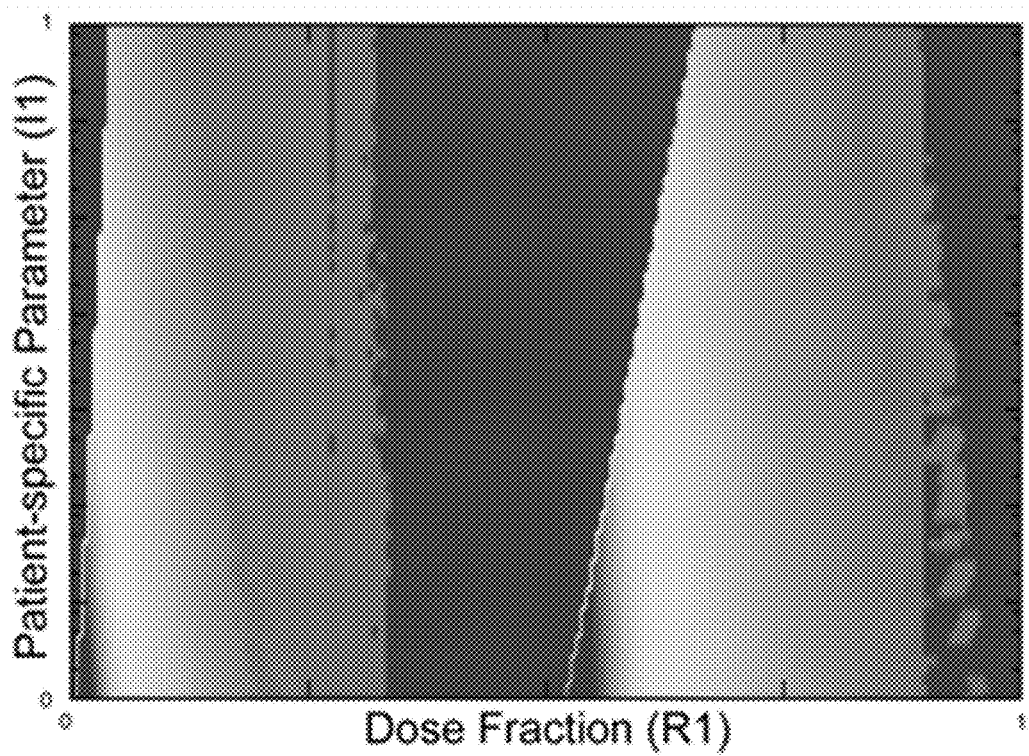
FIG. 6 represents a high-resolution output of the clinical outcome predicted by the module, with a single patient-specific parameter.
Figure 7:
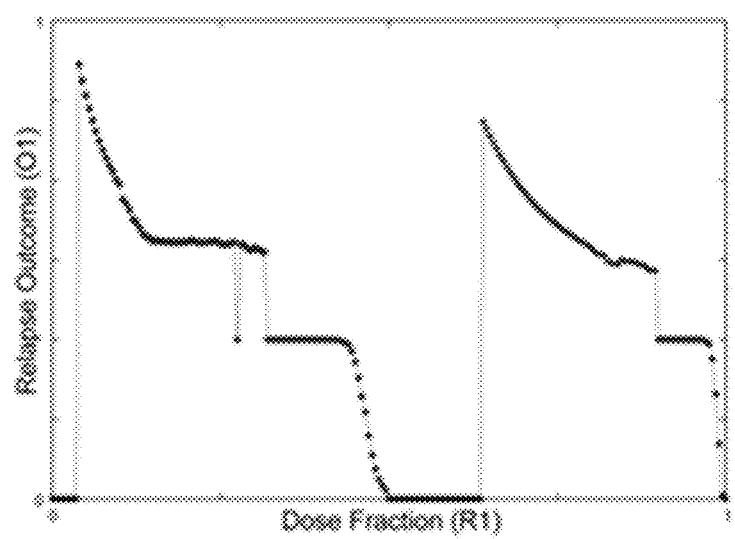
FIG. 7 illustrates a cross section of the output.
Figure 8:
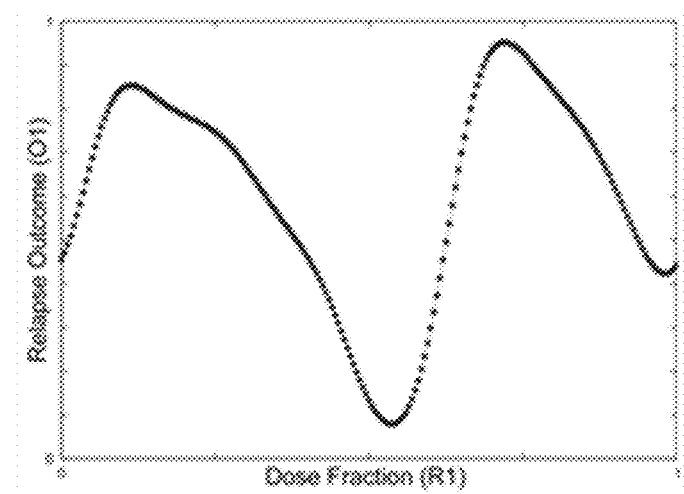
FIG. 8 illustrates the results of a user input.

The optimization process is illustrated in FIGS. 6, 7, and 8 by using a simplified module and framework algorithm to simulate the process. The module used here simulates tumor growth under the application of a treatment that is controlled by a dose fraction parameter, labeled R1. Additionally, the model contains a single patient-specific parameter, labeled I1. FIG. 6 represents a high-resolution output of the clinical outcome (O1) predicted by the module, with I1 on the vertical axis and dose fraction R1 on the horizontal axis. The color output shows the patient relapse outcome for any pair of I1 and R1, with white being the best patient response and black being worst. This model predicts that for any given patient-derived parameter value of I1, there are two choices of R1 that the clinician can use to maximize the positive clinical outcome. This optimal value of R1 depends on the patient-derived value of I1. For a specific value of I1 (0.85 in this example), a cross section of the output is shown in FIG. 7, with best outcomes being positive. The optimal selection for the dose fraction parameter R1 is about R1=0.04, with a secondary maximum at R1=0.64.

FIGS. 6 and 7 represent the ideal situation where a very fine grid of the entire parameter space {I by R} can be explored. Since it is computationally prohibitive to simulate a complex multidimensional model in this resolution, the IVPF will instead find the optimal control values for a series of input parameter values, as described earlier. This information can then be used to derive an outcome function that is the integration of the range of patient-derived input (P), smoothed by the value of a risk-reward slider that mitigates risk for poor therapeutic outcome. For example, if the user inputs a patient-derived range for I1 between 0.7 and 1.0 in the above example, and selects moderate risk-reward, the integration and smoothing algorithm will produce the output shown in FIG. 8, again with best outcomes being positive. The optimum value of R1 has shifted to 0.72, and this is the value that will be the primary recommendation to the clinician. The secondary maximum corresponds to R1=0.11. This can also be given as an option, with a comparison of outcomes for both choices of R1.

The value of the risk-reward slider is best understood by considering the detailed output of FIG. 7. Based on the output of this particular SM, the most successful treatment dose is adjacent to a very steep slope in outcome. However, it would be risky to aim for this dose, since a slight error in dosing would change the outcome from very good to very poor. In other words, there is a high risk to choosing the true optimal therapy, in that very poor outcomes are likely if there is slight error. Upon examining the outcome generated in FIG. 8 after applying moderate risk reward, it is clear that the recommended dose is higher than the true optimum, precisely to minimize the risk that slight errors in dosing will produce drastically different results.

In this example, the risk-reward setting has shifted the optimum recommendations for R1 from about 0.64 to 0.72 and from 0.04 to 0.11. In addition, the best outcome prediction for the two possible therapeutic recommendations has swapped, so that the right peak is more likely to benefit the patient on average. This is because the left peak, while potentially producing a more successful result, has more risk of poor outcome due to uncertainties in therapeutic regimen and patient parameters.

In Phase 4, there is an additional method for refining the patient-specific virtual cohort. By using temporal data generated in the period of time between a patient's initial therapy and subsequent follow-ups, the IVPF can check the predictions made for each simulation in the patient-specific virtual cohort. Armed with temporal follow-up data, the IVPF will discard outcomes of simulations that are not validated by the temporal data. This temporal validation will likely restrict the patient-specific virtual cohort to a smaller, more targeted population, leading to better predictions. From a technical perspective, the algorithm will weigh the outcomes from the temporal simulations according to their temporal fit with the true patient data. The optimization routine will therefore be weighted towards those simulations that best tracked the actual patient progression.

Figure 9:
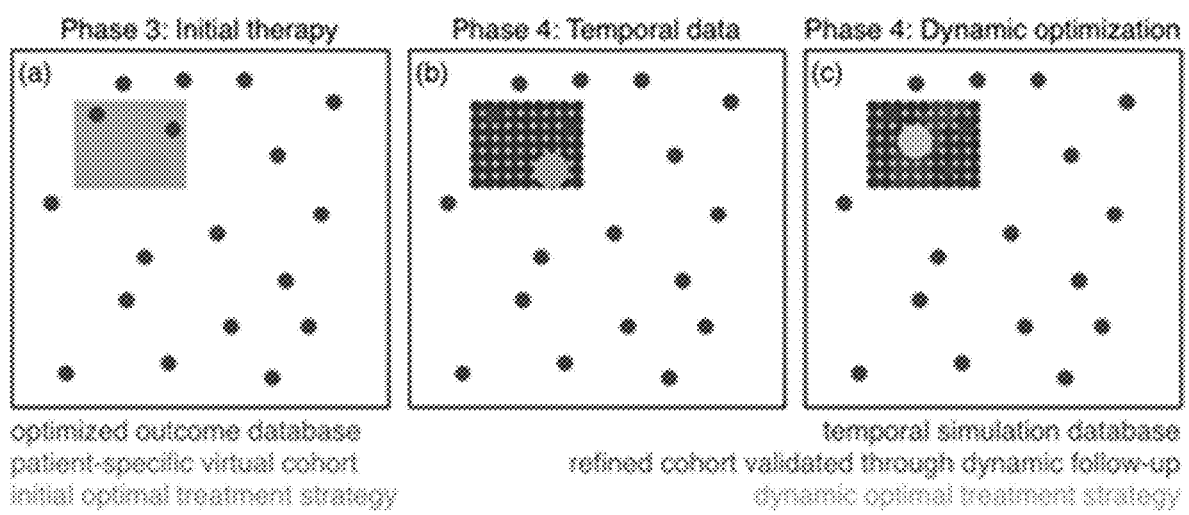
FIG. 9 shows a schematic using databases in combination with the patient-specific virtual cohorts to determine dynamically optimized treatment strategies.

FIG. 9 shows a schematic of how the databases are used in combination with the patient-specific virtual cohorts to determine dynamically optimized treatment strategies. The outcome database (scattered dots in each panel) is populated to cover the entire space of possible patient data. When a patient enters the system, their patient-specific data defines the patient-specific virtual cohort (gray rectangle of panel (a)), determining a subspace of optimization. Layer 3 produces an optimized therapy for the patient (large dot in panel (a)). Immediately, Phase 4 commences. Temporal data for the patient-specific virtual cohort is generated (organized series of dots in panel (b)) and stored. When the patient returns for follow-up, the newly collected patient data is compared to the predictions of the temporal database. Simulations are weighted based on how well they predicted the patient progression, leading to a refined patient-specific virtual cohort (lighter area of the PSVC in panel (c)). This new cohort is optimized for therapy, leading to a new treatment prediction (large dot in panel (c)). The process repeats with each follow-up visit, so that therapy recommendations are adapted based on each new collection of data from the patient.

Figure 10:
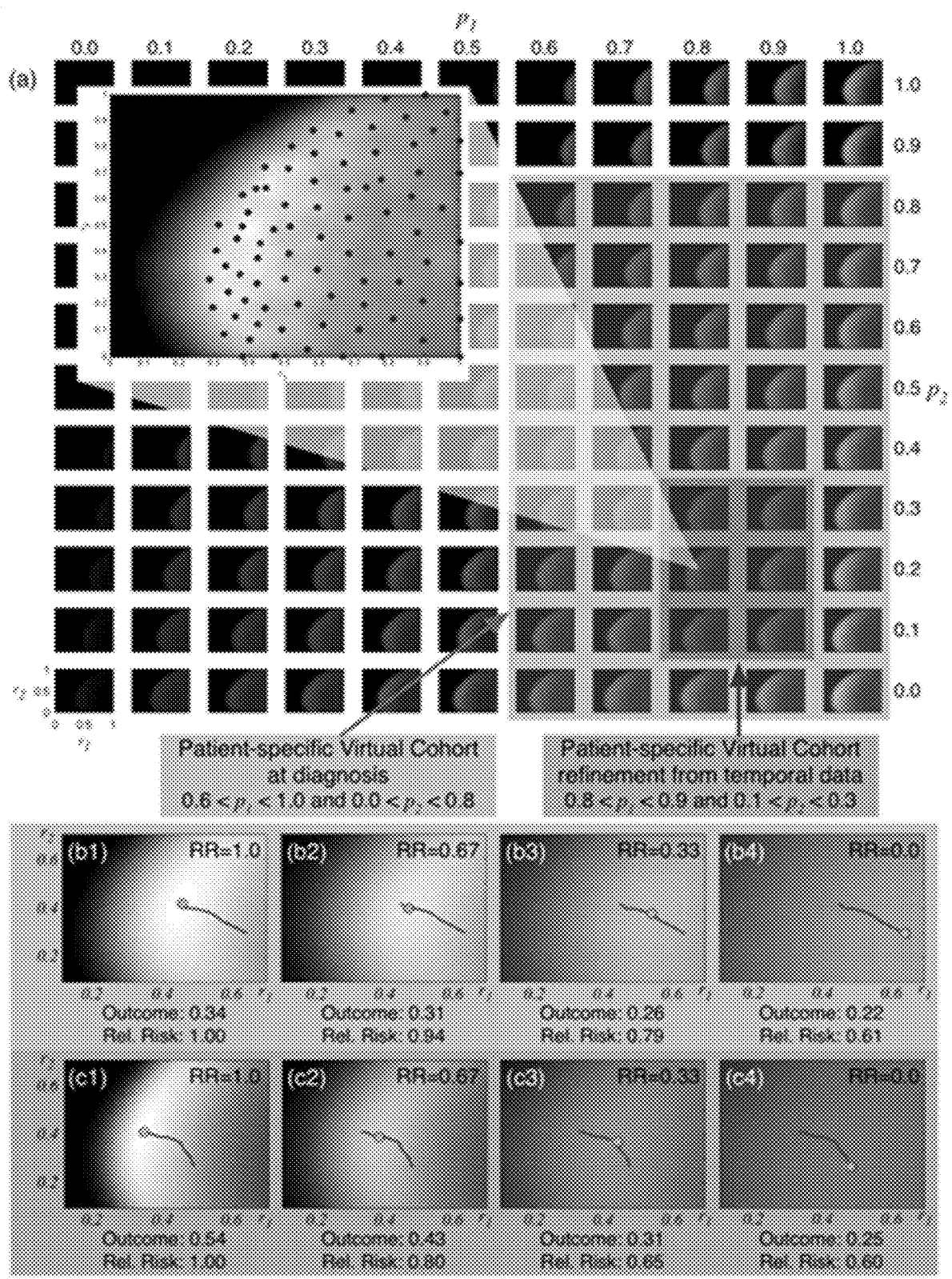
FIG. 10 represents the outcome of running a dynamic treatment optimization on a patient with two measured clinical parameters, and two treatment control parameters.

An implementation of Phase 4 with a SM that uses two patient parameters and two therapy control parameters is shown in FIG. 10, using as an illustration an extended example of the predictive mathematical module described above for the example of Phase 1 and 2. In this extended module, there are two patient-specific parameters, p1 and p2. The parameter p1 represents the ER staining in the biopsy tissue, and p2 represents the percentage of Ki 67 staining. For this sample module, there are two control parameters (r1 and r2) that adjust the delivery regimen of a chemotherapeutic drug in combination with hormone therapy. Control parameter r1 is the dose fractionation, and r2 is the delivery interval. The module output is the tumor burden at one year post-therapy. As in the previous example, all inputs and outputs are normalized to the range of [0,1].

FIG. 10 particularly illustrates the process used by the IVPF in Phase 2 and Phase 3. Panel (a) shows a sample VPD generated using the module described above. The sampling space has a resolution of 0.1 across both dimensions of the parameter space, with values of p1 and p2 shown on the top and right axes of the overall grid. At each sample point, there is a heat map of the reconstructed outcomes over the space {r1×r2} with axes as shown on the lower left map. These heat maps were generated from the data points stored in the virtual patient database (VPD) for each sampling point. The inset shows an enlargement of one heat map for the parameter combination (p1=0.8, p2=0.2) with white areas representing the best outcome and dark areas representing poor outcomes. Superimposed are data points representing the stored VPD data generated by the IVPF in Phase 1.

Suppose that the initial diagnosis for a particular patient found that the level of ER staining (p1) was between 0.6 and 1.0 (in normalized units), and that Ki-67 stain (p2) was at most 0.8. These bounds would be entered into the clinical application and the system would place the patient into the initial diagnosis PSVC shown in the larger of the two outlined rectangles of FIG. 10. The system will then integrate the outcome data in this PSVC to derive the cohort outcome function using the database integration techniques described in the Phase 1. When the integrated outcome function has been derived, this information is returned to the software application to generate an appropriate prediction of the outcome.

Clinical risk-reward adjustment. Once the cohort outcome function is calculated, the clinician can interact with the suggested outcomes by adjusting a risk-reward (RR) slider. The purpose of this particular clinical adjustment parameter is to inform the clinician about the confidence of the derived predictions and their sensitivity to variance in the measured patient and therapeutic parameters. When the risk-reward slider is set to high-risk high-reward, the optimization algorithm will favor those therapies that have the best possible outcome out of all therapeutic options, without consideration of the sensitivity of this outcome to variations in parameter values. When the slider is set to low-risk low-reward, the optimization algorithm will find the best therapy that minimizes the risk of poor outcomes due to parameter variations. The implementation of the RR slider in this particular case can be accomplished by using, for example, Gaussian smoothing across the parameter dimensions and then deriving the optimum treatment from the smoothed outcome function. There can be multiple risk-reward sliders to cover different clinical contingencies. For example, drug efficacy, drug toxicity, patient compliance, and impact of other co-morbidities can have risk-reward sliders that interact.

This output generated by this RR process is illustrated in FIG. 10, panels (b1-b4). The integrated outcome data from the initial PSVC from FIG. 10, panel(a) are shown for four values of the RR slider. Panel (b1) shows the high-risk high-reward setting. Here, the algorithm has selected the best overall therapeutic option for the PSVC, leading to a cohort-wide average outcome of 0.34. The suggested optimal combination of treatment parameters (r1=0.45, r2=0.41) is shown by the open circle. However, the region of very poor outcomes (dark area) on the left side of the heat map suggests that there is some risk of a bad result from therapy if there is some variation in the true parameters. As the RR value is lowered in subsequent panels, the recommended therapy travels along the line, away from the area of poor outcome. The corresponding cohort average outcome values decrease, as do the associated risks. The low-risk therapy suggestion (r1=0.64, r2=0.3) in panel (b4) will have a lower chance of a good outcome, but also a lower chance of a poor outcome. In this particular example, the asymmetry of the outcome landscape leads to changes in optimal therapy recommendation as a function of the RR value. Other models that have more symmetric outcome landscapes may see very little shift in recommended therapy. Having explored the RR settings, the clinician would be able to use the results from the IVPF to inform the actual therapy delivered to the patient. Once a treatment course is decided, this selected therapy would be input into the interface application for use in the Phase 3.

Phase 3 implementation. When a clinician inputs the chosen therapy at the end of Phase 2, the IVPF will call on the mathematical module to generate patient-specific temporal data for later comparison with actual patient follow-up data. The IVPF will fix the treatment parameters (e.g. r1, r2) to those that were selected for the patient. The system will then call on the mathematical module to simulate temporal data across a sampling space of the initial PSVC (large rectangular outlined area of FIG. 10). This data will be stored in the VPD, with a temporal resolution appropriate to the follow-up conventions of the particular disease. For example, a disease with expected follow-up frequency on the order of one year will not need the same temporal resolution as one that is managed on a weekly basis. Since the return date of the patient may not be precisely specified at the time of initial therapy, the temporal database will store a time series of all variables and outcome metrics in the module for each sample in the PSVC. The resolution of the sampling space of the PSVC will be determined by the computational power available to simulate the temporal database in quasi-real time. Since the temporal data will be used only at the time of follow-up, there is no need to simulate far beyond the real elapsed time since patient therapy began. In other words, if it has been 50 days since the patient began treatment, all simulations in the temporal DB for that patient will have been simulated out to 50 days, plus some cushion. This maximizes computational efficiency and also gives the highest sampling resolution subject to computational power.

At the time of follow-up, new data will be collected from the patient. The clinician would return to the interface app, enter the virtual patient ID, and then input the appropriate follow-up data. The IVPF will compare this patient data with the simulated temporal data evaluated at the actual follow-up time. For example, if a patient returns after 60 days, then the simulation outcomes are queried for t=60 within the temporal database. The comparison of simulated and patient data will generate a weight for each parameterization in the sampling space of the PSVC. Some simulations will match well, and these will be assigned a higher weight. Simulations that poorly predicted the follow-up data will have a lower weight. Once this weighting is determined, the IVPF will then refine the PSVC by including these weights in the follow-up recommendations. Using the example above, suppose that the simulations in the range of (0.8<p1<0.9, 0.1<p2<0.3) were well matched with the actual follow-up data, while simulations outside of this range were poor predictors of progression. Then the IVPF would effectively define a new refined PSVC through a weighting function that gave weight only to the simulations in that range. This new PSVC is indicated by the smaller outlined rectangle of FIG. 10, panel (a). For clarity here we have given full weight to these simulations and no weight to simulations outside of that range. In practice, the entire range will have continuous weighting applied to it.

The use of this weighting will be included in the data integration process (as described in Phase 1 and Phase 2) to derive a new prediction of follow-up therapy. FIG. 10, panels (c1-c4) shows the outcomes for four values of the RR slider for the weighted outcomes from the refined PSVC. Again, the therapy recommendation changes with different RR. Of interest is that the expected outcomes have improved compared to the initial therapy recommendations of FIG. 10, panels (b1-b4). For the high-risk setting, the average cohort outcome has increased from 0.34 to 0.54. This is due to the fact that the temporal data fitting has narrowed the size of the effective PSVC so that new predictions can be better tailored to the patient. The Phase 3 can be repeated as necessary with each patient follow-up visit. Increased data collection subsequently leads to more personalized, dynamically optimized treatment in the clinic.

Figure 11:
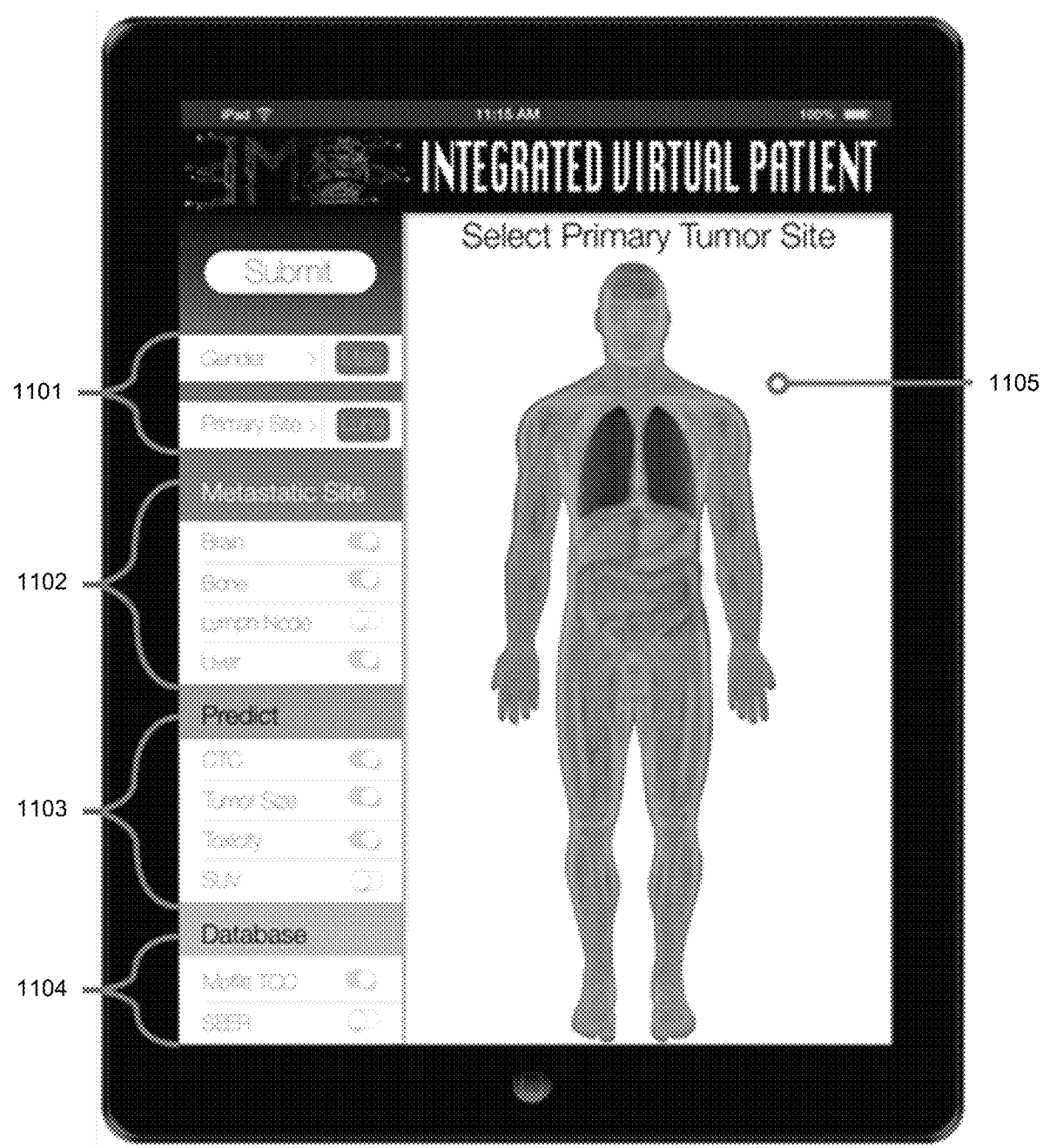
FIGS. 11 and 12 illustrate user interfaces of a clinical application.

In Layer 4, the clinical interface Application 126 may be a software application (app) is a multi-platform tool that allows a clinician to interface with the IVPF, using the system to get personalized results for an individual patient. Designed to use minimal resources locally (calling pre-stored information remotely) and therefore capable of running on almost any mobile device e.g. Tablet computer or smart phone. The front end of the app, shown in FIG. 11, will be where the clinician chooses the modules specific to the disease as well as the optimization criteria. In FIG. 11, 1101 is a patient gender and disease site selection, 1102 is a metastatic site selection, 1103 are module specific output options, 1104 is a selector for a choice of historic Databases for validation purposes and 1105 is a touch sensitive interface allows direct choice of primary disease site and metastatic sites.

Figure 12:
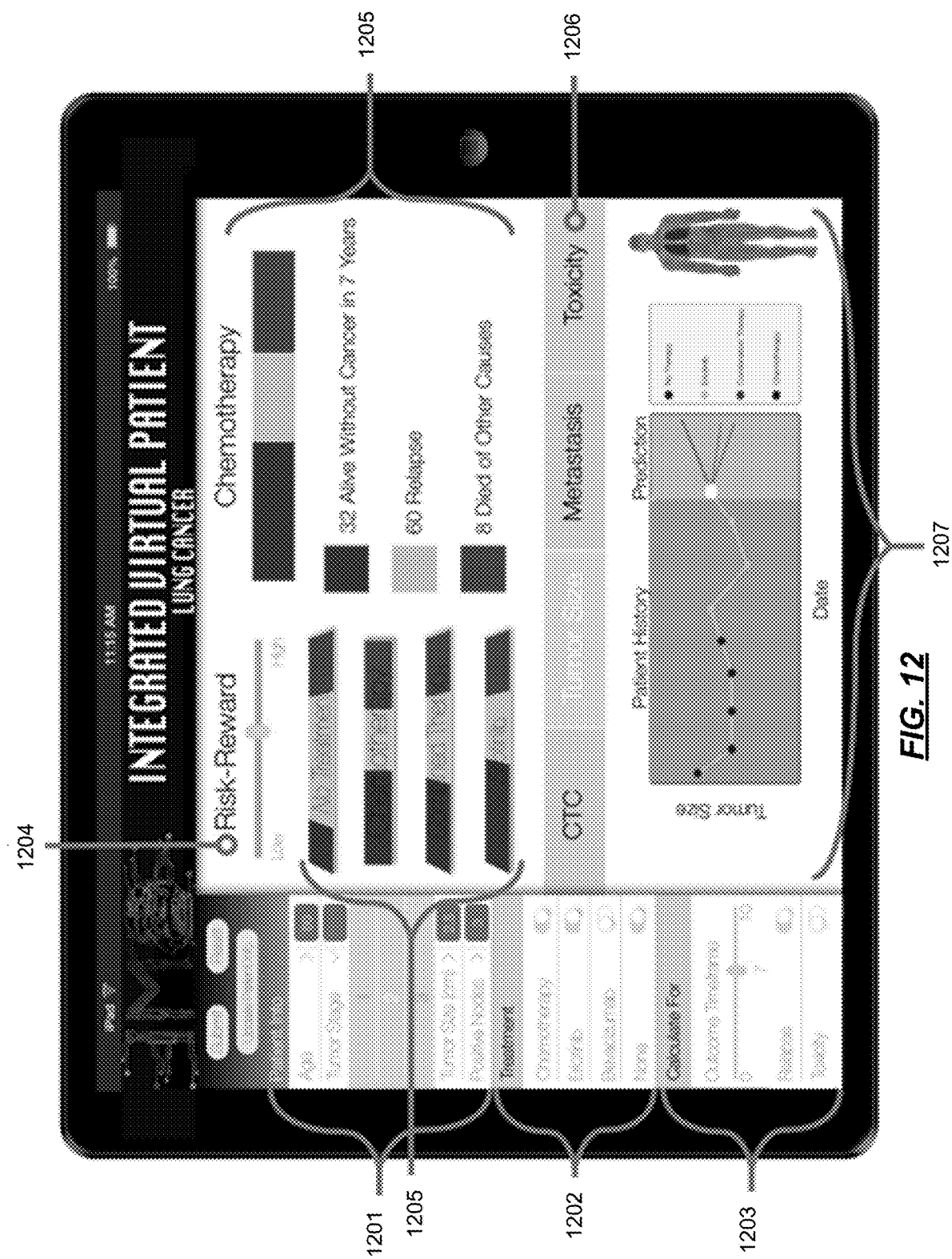

The clinical interface, shown in FIG. 12, is where the clinician inputs the patient-specific data, therapeutic restrictions, and further optimization criteria. In FIG. 12, 1201 is a patient data input, wherein multi-level drop downs ties to specific disease site, Reference 1202 are disease specific therapy options, 1203 are optimization criteria, 1204 is one or more risk-reward sliders allowing the clinician to weigh the trade off between predicted/actual therapeutic success due to uncertainties in patient care. Reference 1205 shows therapeutic optimization results, where the left panel shows range of treatment options and relative outcomes and the right panel shows a larger version of the most successful strategy. Reference 1206 is a module output selection, where different predicted outcomes can be visualized. Reference 1207 is a module specific output—visualization of outcomes both historic and predicted may be shown.

The inputs from the interface are sent to the IVPF, which will quickly analyze the data from the VP database, subject to the constraints input by the clinical user. The results from the IVPF are then displayed here, and adjustment of the clinical risk-reward slider(s) will shift the outputs appropriately. The clinician would be able to page through all associated outcome data from the simulated results.

EXAMPLE APPLICATIONS

Briefly outlined below are two examples of how the framework may be applied to specific diseases in the clinic. These examples are not limiting, since the framework is broadly applicable to a range of problems, but rather serves as an illustration of actual applications. Any decision system that can be quantified by an optimization metric and parameterized by measurable inputs would function within the framework.

Example (i): Risk Prediction in Large Granular Lymphocytic Leukemia (LGLL)

In LGLL, patients would benefit from the ability to estimate the severity of progression of the disease after diagnosis. At present, the approach used is "watch and wait," in which the clinician will wait until the disease begins to rapidly progress before giving treatment. However, this is often not the optimal time for therapy, it being administered too late. Being able to track and model patients in the clinic so that the onset of aggressive disease can be predicted would allow preemptive therapy to be given before the disease progresses too far.

In order to use the IVPF framework, first a mathematical model of LGLL would be developed. This could include various disease relevant patient-specific inputs, such as blood cell counts and other blood biopsy measurements; ex-vivo cell culture experiment results providing dynamic information on T-cell replication rates; bone marrow biopsies to measure fibrosis; etc. The clinical control parameters could initially be limited to a binary decision of whether to treat or not treat. The optimization criteria would be some clinically relevant measurement of diseased clonal T-cells, perhaps combined with metrics of other symptoms such as cytopenia.

Once the module was developed, it would go through the four phases of the IVPF:

Phase 1: The model would be validated against LGLL patient-databases, of which several exist in the United States. Proceed to next phase once validated.

Phase 2: The outcome database would be generated.

Phase 3: Would begin to aggregate patient data with implementation into the clinic. The outcome data would be a prediction of risk of aggressiveness without therapy. Using this output for a given patient, the decision to treat or wait would be made by the clinician. I.e., patients with low risk for aggressive disease would be placed on "watch and wait," while those that the IVPF predicted high aggressiveness would receive therapy at once.

Phase 4: Subsequent visits by the patients on the "watch and wait" plan would generate new blood biopsies which would be analyzed for patient progression. These new data would be used to refine the subset of progression simulations that the patient satisfied. This would lead to a new metric of aggressiveness. In particular, the IVPF would be able to indicate which patients that were on the "watch and wait" plan were becoming more aggressive (i.e., time to treat) and which remained indolent (continue to "watch and wait").

Example (ii): Optimize Adjuvant Therapy for Breast Cancer Patients without Known Metastases Many patients with primary tumors of the breast do not have detectable metastases at the time of diagnosis and initial therapy. However, a subset of these patients do relapse with distal metastases after some period, even with application of adjuvant therapies post-surgery. A pressing question in the clinic is what is the best type of adjuvant therapy to administer for patients that have no distal metastases on initial scans. There are various hormonal therapies, chemotherapy, radiation, and targeted therapies, all of which can be combined in various ways. Without any residual disease detectable, there is no way to optimize therapy based on metastatic biopsies.

To use the IVPF framework to address this question, a model of metastatic growth of breast cancer cells in various distal sites (bone, brain, lungs) would be developed. The models would simulate the effects of various clinically relevant treatments. Relevant parameters would be principally derived from the primary tumor, including the status of hormones, metabolic and growth markers, and other relevant molecular properties. Toxicity would be part of the model. Clinical control parameters would be the selection and durations of therapies. Optimization criteria would be the minimization of potential metastatic growth.

Once the module was developed, it would go through the four phases of the IVPF, as follows:

Phase 1: The model would be initially validated against the database of breast cancer patients, both with and without metastatic relapse. The therapies would be SOC, and outcomes would have to match the historical record. Proceed to next phase once validated.

Phase 2: The outcome database would be generated.

Phase 3: Patients initially diagnosed with primary breast cancer would have their biopsies analyzed to produce patient-specific data. The IVPF would process this data to find an optimal therapy recommendation that would minimize the chance of metastatic recurrence without causing undesired toxicity.

Phase 4: Subsequent visits by the patients would include scans for metastatic cancer. In addition, any relevant physiological measurements, for example hormonal levels and toxicity responses to the drugs, could be used to check model predictions. Patients that scanned clean would have new temporal data on toxicity symptoms that could lead to therapy adjustments.

Other Applications

With some modifications to the clinical interface application, the IVPF could be used with any disease where predictions of risk and outcomes are valuable in determining a course of action for the patient. This would not be limited to cancer; indeed it is hard to imagine a disease where patient-data would not be useful for predicting outcome. The IVPF can operate on any timescale, so acute infections lasting a matter of days are as tractable as chronic diseases that persist for decades. Due to the modular nature of the framework, any mathematical model that satisfies the conditions of input and output data can be used. Therefore, the IVPF could be used for problems outside of the biomedical field as well, although some changes to the interface app might have to be made to match the specific needs of the field in question.

It is possible to only measure a limited amount of biology for any given patient and it is impossible to simulate a true representation of a specific patient—the VPD resolves these issues by using a hybrid approach that represents a single real patient with a cloud (cohort) of similar patients. The accuracy of this cohort will improve significantly the more the VPD is enriched, with patient specific virtual cohorts, refined by true temporal data gathered from individual patients. At this point analysis of the virtual cohorts for a given disease will reveal novel aspects of the disease that can only be obtained through our IVPF approach. Specifically, this analysis may lead to new diagnostic techniques, new therapeutic strategies, novel biological associations and mechanistic interactions. Furthermore, such analysis also applies across different VPDs and may indicate additionally novel commonalities.

Furthermore, the database and analysis tools generated in the process of using the system in a clinical setting are a valuable resource for use in subsequent clinical trials. The IVPF can be used to design virtual clinical trials, in which millions of virtual patients can be tested for key diagnostic markers, toxicity, and efficacy of existing and novel compounds. With an appropriately modified SM to address the novel therapeutic approaches to be investigated by the Phase I trial, the IVPF can run a Phase "i" trial. These results could assist trial designers in cohort selection, therapy regimen strategies, and also predict the potential risks faced by administration of the trial. The power of this approach would be extended by the use of a validated VPD that had been refined by machine-learning algorithms during the acquisition of real patient data.

Decision Support Via Evolutionary Model Analysis

The framework of the present disclosure may be used to provide decision support that evolves in conjunction with the increasing data collected on a given patient. Patient data occurs at varying resolutions. For example, at the beginning of their clinical trajectory, the information is sparse, often a single time point at diagnosis. As the patient is treated, additional timepoints are received. These data can be acquired based on standards of care, or through specific decisions from the oncologist such that the use of patient data changes through a course of therapy.

Figure 13:
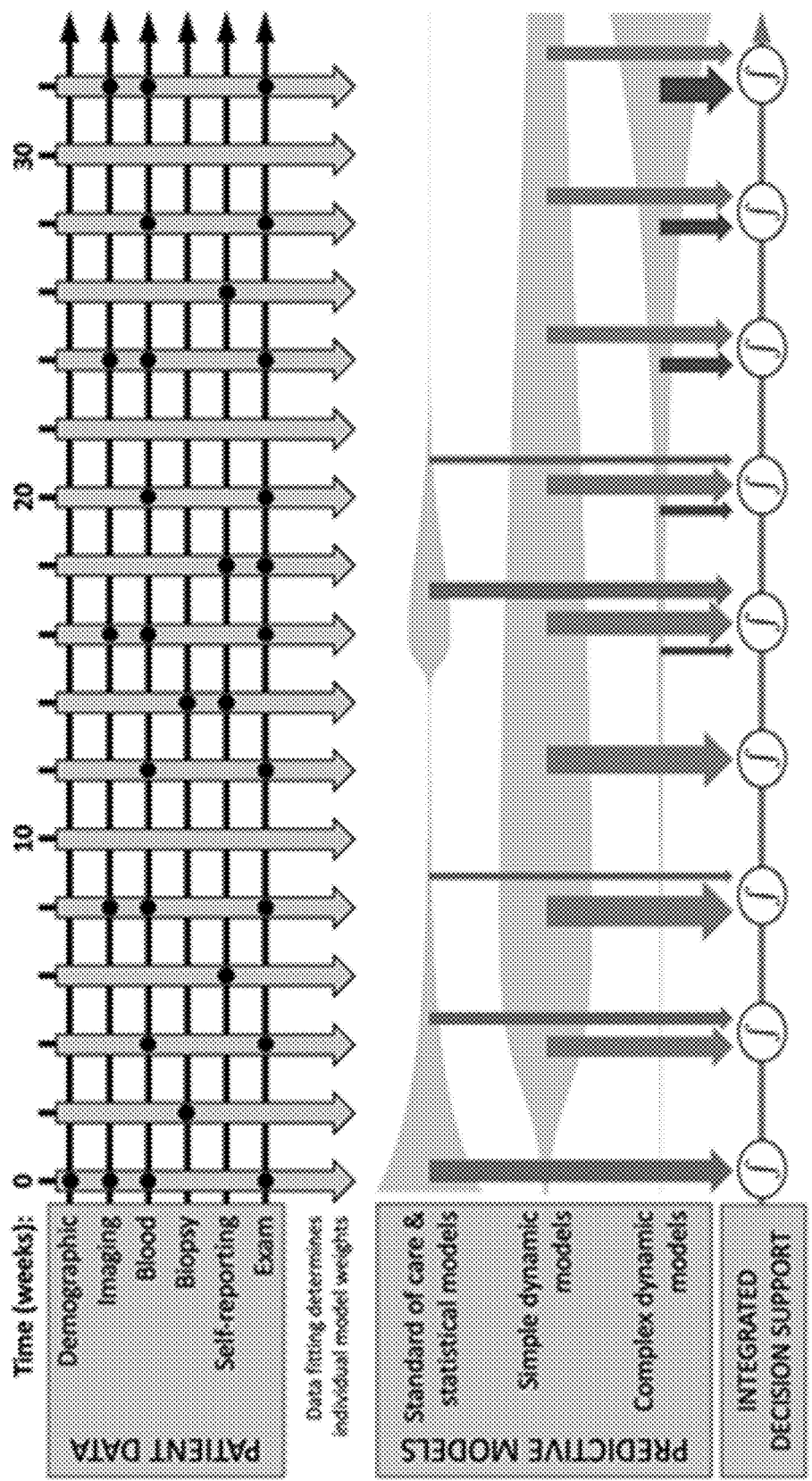
FIG. 13 shows a time of patient data and the evolution of models from statistical models to dynamic models.

With reference to FIG. 13, patients with single time point data (left edge of figure) may be limited to support using statistical prediction tools derived from historical cohorts of similar patients, where similar is defined by one or more biomarkers or demographic information. Later in the patient's treatment, there may be a few temporal data points (central section of figure) that are feasibly modeled with simple mathematical models that can constrain the possible dynamics of the patient. Patients with longer histories or denser biomarker measurements (towards the right edge of the figure) benefit from a more detailed predictive model, since different types of data are integrated and better fitting of the data is possible.

Thus, the framework uses multiple models, ranging from statistical to mechanistic, and evolves the predictive decision support based on new data as it is collected from the patient. Two or more models, including but not limited to statistical, machine learning, AI, mechanistic, and hybrid models may be used. Weights for each model are assigned depending on uncertainties arising from data fitting and model properties, e.g. models with better fits will have a higher weight.

As new data are entered into the patient record (e.g., the dots in FIG. 13), the models are recalibrated and the weights are adjusted, leading to updated decision support information (connecting arrows between models and Rx decision support). The framework also may suggest the benefit of additional follow-up data collection events, in essence optimizing the data collection (with constraints) as well as how it generates predictions.

Patient Education and Empowerment Application

A direct benefit of the framework is that it can be used to present scenarios to patients in a way that informs them of treatment outcomes, given various strategies. This can be done via, e.g., an app that describes the range of outcomes and risk-reward considerations for each treatment strategy that is under consideration. Patients may explore different dosing and schedule changes to see potential impacts to their disease course. This has the added benefit of educating the patient as to the impact of a specific treatment strategy as well as empowering them to suggest specific strategies for their care. It would also serve as a real time update of a patients progress on a given treatment protocol.

Integration of Personal Health Data

With poor temporal density of follow-up visits being an issue in oncology, collection of any additional data from patients can be useful as a method to increase the accuracy of predictive models. The appearance of symptoms that might indicate disease progression, or treatment toxicities, would be reported by the patient and this can be added to the collection of data for the patient, and enhancing the prediction of the decision support tool. This type of data could be directly entered via the interactive app that the patient used to monitor their treatment and play out different treatment scenarios.

Figure 14:
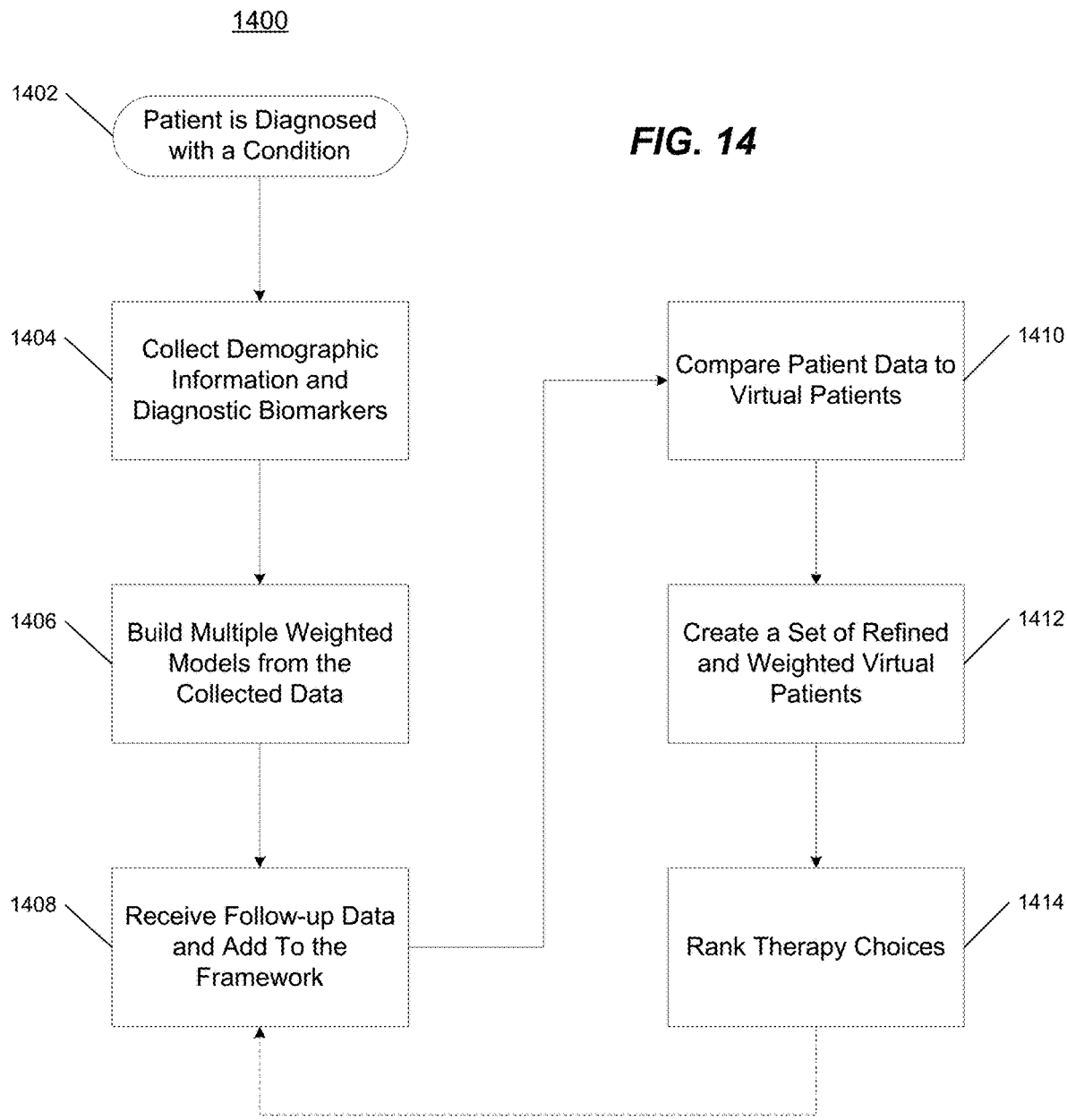
FIG. 14 illustrates an example workflow of the evolution of the models in accordance with patient data.

FIG. 14 illustrates and example workflow 1400, which begins with a patient being is diagnosed with a condition, e.g., cancer, at time 0 (1402). At 1404, demographic information is collected, along with various diagnostic biomarkers (including but not limited to: imaging, blood, biopsies, physical exams, patient self-reporting, genetic analysis, etc.), and this information is provided to the IVPF framework.

At 1406, multiple models are built for the particular disease that use different aspects of the data that are collected to generate predictions of how the patient may respond to the available therapy options at the start of treatment. In general, these models will be statistical models as there are few temporal data points and these will have the highest weight at the start of the patient's course of therapy. At this stage, dynamic models, which generally require multiple time points to generate fitting constraints, will likely have lower weights at diagnosis. The initial data may restrict some of the parameters of the dynamic models, which allows for the IVPF to commence analysis of potential trajectories for the patient, generating stored Virtual Patients in the Virtual Patient Database. This is done independently for each distinct model used for the particular disease. The statistical predictions delivered by each model are weighted depending on the uncertainty produced by each model, and the choices of therapy are ranked and delivered to the treating physician along with associated supporting information such as: the likelihood of successful outcome for each; the statistical uncertainties in the predictions; trajectories of possible outcomes.

At 1408, after therapy commences, follow-up data is received that is added to the IVPF framework. Typically, a point in time is reached where the patient may be eligible to alter their therapy or continue with the current therapy. At this point, the patient's collected data is compared against the large number of virtual patients that exist in the database of simulations, by collecting the same type of data from each virtual patient (if available for that particular type of model) as was collected from the patient themselves, at corresponding timepoints in each simulation (1410). This is done for each of the one or more dynamic models used for the particular disease. For each model and its associated virtual patients, some simulations will match the change in the collected biomarkers better than others, and the IVPF will weigh the virtual patients for each model accordingly, to generate a cloud of similar virtual patients and discard those that don't match the available data.

At 1412, a set of refined and weighted virtual patients for each model is created by this process. These refined cohorts of virtual patients are then subjected to "Phase i" trials (each set as a virtual patient cohort). For each model and virtual patient cohort, this virtual "Phase i" trial subjects the virtual cohort to each available treatment possibility (e.g., continue current therapy, add an agent, have a treatment break, switch to an alternative agent or agents, stop the therapy altogether, etc.). The framework associates an uncertainty to the results based on the range of outcomes observed in the virtual trial (because each virtual patient reacts differently to the administered therapy). These predictions from the different virtual trials run using each different model are then integrated together using new weighting that is based on the uncertainties generated from the virtual trials. The weight of each model-generated virtual trial changes independently based on the prediction uncertainty arising from the model fits and parameterizations. The evolution of these weights allows continuous refinement of the IVPF predictions, and furthermore allow 'unexpected' data to be accounted for by different models.

In an example application, many aspects of cancer growth are stochastic, and therefore can arise at unpredictable times. For example, a cancer mutation may cause a significant change in tumor dynamics and/or response to therapy. In this case, one or more models may be developed to simulate the dynamics of the tumor pre-mutation, and one or more models may be developed for the dynamics post-mutation. As patient data is received, the data may fit the first class of models for a time and not the second class; after some time and the acquisition of additional data, there may be a change in the dynamics that fits the second class of model(s) better, and less so the first class. The IVPF can adjust weights for these models based on how the models fit at each given decision point, as well as directly collected data (e.g., if a biopsy confirms the mutation). Therefore, the patient acquiring the mutation may lead to the weights shifting from favoring one set of models to favoring a different set. This evolution can then potentially alter the outcome of the therapy decision support recommendations.

In another example application, some models may be developed for certain aspects of the disease rather than the disease as a whole; for example, metastasis to different sites in the body (e.g., bone, lungs, brain) may require different models, and these different models may be weighted depending on whether metastatic lesions are found in the particular sites from patient scans. Alternatively, or in combination with patient data, the weighting can also be based on historical statistical data regarding the likelihood of metastatic dissemination occurring in different sites. These likelihoods can change over time in the historical record, and this can alter the weights of the different models over time. For example, the likelihood of seeing metastatic lesions in one site may decrease with time on some therapy; therefore, the model(s) that simulate the growth of lesions in one site will be given successively less weight over time if the patient's data doesn't show evidence of lesions at the site.

At 1414, therapy choices are ranked based on the outcome of the IVPF analysis and delivered to the treating physician. The ranking may be done through an application where a physician may be presented the available therapies, the likelihood of successful outcome for each, the statistical uncertainties in the predictions, and trajectories of possible outcomes, as examples. Other options may be presented. The physician may change certain aspects of the optimization, including but not limited to: restricting or expanding the types of therapies available adding or removing the considerations and constraints regarding treatment selection such as drug toxicity, payer status, financial toxicity; altering the outcome metrics that are considered in the optimization such as overall survival, progression-free survival, minimize toxicity, and/or combinations of these; altering the risk-reward level for one or more aspects of risk related to one or more therapy options. Toxicity biomarkers, payer coverage, and financial aspects of therapy can be included in the decision support vector at any time In accordance with an aspect of the disclosure, steps 1408-1414 may be repeated, as necessary, for example, each time that new patient data is collected. In this manner, the virtual patient database is continuously updated and added to, along with the associated weights for each virtual patient in each model. New patients are generated by prioritizing the branches in the virtual patient cohort that best match the patient data (i.e. have higher weights), and minimizing simulations along trajectories that have low weights. This pre-simulation is a key aspect of being able to deliver decision support rapidly when new patient data arrives.

Figure 15:
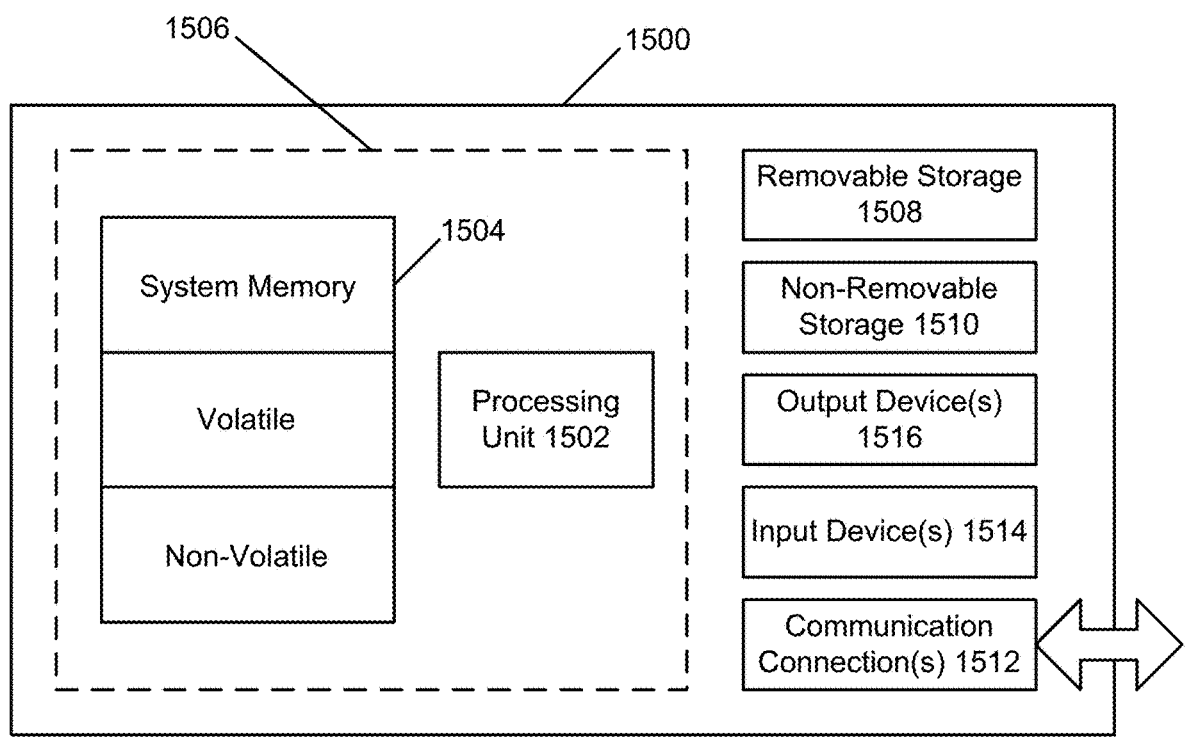
FIG. 15 shows an example computing environment.

FIG. 15 shows an exemplary computing environment in which example implementations and aspects may be implemented. The computing system environment is only one example of a suitable computing environment and is not intended to suggest any limitation as to the scope of use or functionality.

Numerous other general purpose or special purpose computing system environments or configurations may be used. Examples of well-known computing systems, environments, and/or configurations that may be suitable for use include, but are not limited to, personal computers (PCs), server computers, handheld or laptop devices, multiprocessor systems, microprocessor-based systems, network PCs, minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that performs particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

An exemplary system for implementing aspects described herein includes a computing device, such as computing device 1500. In its most basic configuration, computing device 1500 typically includes at least one processing unit 1502 and memory 1504. Depending on the exact configuration and type of computing device, memory 1504 may be volatile (such as random access memory (RAM)), non-volatile (such as read-only memory (ROM), flash memory, etc.), or some combination of the two. This most basic configuration is illustrated in FIG. 15 by dashed line 1506.

Computing device 1500 may have additional features/functionality. For example, computing device 1500 may include additional storage (removable and/or non-removable) including, but not limited to, magnetic or optical disks or tape. Such additional storage is illustrated in FIG. 15 by removable storage 1508 and non-removable storage 1510.

Computing device 1500 typically includes a variety of computer readable media. Computer readable media can be any available media that can be accessed by device 1500 and include both volatile and non-volatile media, and removable and non-removable media.

Computer storage media include volatile and non-volatile, and removable and non-removable media implemented in any method or technology for storage of information such as computer readable instructions, data structures, program modules or other data. Memory 1504, removable storage 1508, and non-removable storage 1510 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1500. Any such computer storage media may be part of computing device 1500.

Computing device 1500 may contain communications connection(s) 1512 that allow the device to communicate with other devices. Computing device 1500 may also have input device(s) 1514 such as a keyboard, mouse, pen, voice input device, touch input device, etc. Output device(s) 1516 such as a display, speakers, printer, etc. may also be included. All these devices are well known in the art and need not be discussed at length here.

It should be understood that the various techniques described herein may be implemented in connection with hardware or software or, where appropriate, with a combination of both. Thus, the processes and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be affected across a plurality of devices. Such devices might include PCs, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implem.

What is claimed:

1. A model-based method for therapeutic decision support in an Integrated Virtual Patient Framework (IVPF), comprising:
    defining a first disease-specific model, and one or more additional disease specific models that provide therapeutic decision support in accordance with a temporal relationship with multiple timepoints for a patient diagnosed with a condition;
    determining, by a computing device, in accordance with each set of patient data at given timepoints, a first therapeutic decision by applying a first weight to the first disease-specific model, a second weight to the second disease-specific model, and subsequent weights to the additional disease-specific models;
    ranking, by the computing device, therapy choices of the first therapeutic decision in a user interface;
    thereafter, repeating by the computing device, for subsequent patient data received by the IVPF:
        adjusting the first weight, second weight and additional weights in accordance with the types of subsequent patient data received;
        comparing the subsequent patient data to virtual patent data in a database of simulated outcomes determined using the first disease-specific model, the second disease-specific model, and additional disease-specific models;
        determining, in accordance with the comparing, a subsequent therapeutic decision by applying an adjusted first weight to the first disease-specific model, an adjusted second weight to the second disease-specific model, and additional adjusted weights to the additional disease-specific models; and
        ranking subsequent therapy choices of the subsequent therapeutic decision in the user interface to provide for continuous refinement of the subsequent therapeutic decision; and
    determining, by the computing device, an optimal outcome based on the subsequent therapy choices.

2. The method of claim 1, further comprising comparing simulated outcomes determined using the first disease-specific model, the second disease-specific model or the additional disease-specific models with historical outcomes for actual patients.

3. The method of claim 1, further comprising adjusting the first weight, second weight and additional weights in accordance with the types of subsequent patient data received each time the subsequent patient data is received.

4. The method of claim 1, wherein the first disease-specific model is a statistical model, the second disease-specific model is a simple dynamic model, and the third disease-specific model is a complex dynamic model.

5. The method of claim 4, wherein the first therapeutic decision is substantially determined in accordance with the statistical model.

6. The method of claim 4, wherein subsequent therapeutic decisions are substantially determined in accordance with a combination of the simple dynamic model and the complex dynamic model.

7. The method of claim 1, further comprising:
    receiving inputs in the user interface to alter aspects of the subsequent therapy choices;
    parsing the simulated outcomes in the database; and
    comparing the subsequent patient data and the altered aspects of the subsequent therapy choices to the virtual patent data in the database of simulated outcomes; and
    updating the subsequent therapeutic decision in accordance with the altered aspects.

8. The method of claim 1, further comprising discarding simulated outcomes that do not match the subsequent patient data.

9. The method of claim 1, further comprising determining at least one of the first therapeutic decision and the subsequent therapeutic decision in accordance with patent data that was acquired before the patient was diagnosed with the condition.

10. A model-based method for therapeutic decision support in an Integrated Virtual Patient Framework (IVPF), comprising:
    receiving, by a computing device at a first time, first data associated with a patient;
    defining at least two disease-specific models that provide the therapeutic decision support in accordance with a temporal relationship with the first time and a second time;
    determining, by the computing device, an initial therapeutic decision by applying weights to a first disease-specific model of the at least two disease-specific models;

receiving, by the computing device at a second time later than the first time, second data associated with the patient;

determining, by the computing device, a subsequent therapeutic decision by:

comparing the first data and the second data to virtual patients stored in a database of simulations performed in using the at least two disease-specific models;

applying weights to the virtual patients to generate a cloud of similar virtual patients to the patient for each of the at least two disease-specific models; and subjecting the similar virtual patients to a trial process using available treatments to determine a range of outcomes;

receiving, by the computing device, subsequent second data;

adjusting, by the computing device, the weights of the virtual patients in response to receiving the subsequent second data;

ranking, by the computing device, subsequent therapeutic decisions associated with the outcomes in a user interface to provide for continuous refinement of the subsequent therapeutic decision; and determining, by the computing device, an optimal outcome based on the subsequent therapy choices.

11. The method of claim 10, further comprising comparing the range of outcomes with historical outcomes for actual patients.

12. The method of claim 10, wherein the first disease-specific model is a statistical model, the second disease-specific model is a dynamic model.

13. The method of claim 12, wherein the first therapeutic decision is substantially determined in accordance with the statistical model.

14. The method of claim 12, further comprising varying dynamic model from a simple dynamic model to a complex dynamic model as time progresses forward.

15. The method of claim 14, wherein subsequent therapeutic decisions are substantially determined in accordance with a combination of the simple dynamic model and the complex dynamic model.

16. The method of claim 15, wherein the simple dynamic model comprises one or more simple dynamic models, and wherein the complex dynamic model comprises one or more complex dynamic models.

17. The method of claim 10, further comprising:

receiving inputs in the user interface to alter aspects of the subsequent therapy choices;

comparing the subsequent patient data and the altered aspects of the subsequent therapy choices to the virtual patent data in the database; and updating the subsequent therapeutic decision in accordance with the altered aspects.

18. The method of claim 10, further comprising presenting, for each of the subsequent therapy choices, a likelihood of a successful outcome, a statistical uncertainty, and trajectory of possible outcomes.

19. The method of claim 10, further comprising presenting scenarios the patient in the user interface to informs the patient of treatment outcomes, given various strategies.

* * * * *